United States Patent
Kumano et al.

(10) Patent No.: US 10,030,023 B2
(45) Date of Patent: Jul. 24, 2018

(54) MERCAPTOALKYLGLYCOLURILS AND USE OF SAME

(71) Applicant: SHIKOKU CHEMICALS CORPORATION, Kagawa (JP)

(72) Inventors: Takeshi Kumano, Kagawa (JP); Takuma Takeda, Kagawa (JP); Noboru Mizobe, Kagawa (JP)

(73) Assignee: SHIKOKU CHEMICALS CORPORATION, Kagawa (JP)

( * ) Notice: Subject to any disclaimer, the term of this patent is extended or adjusted under 35 U.S.C. 154(b) by 0 days.

(21) Appl. No.: 15/038,128

(22) PCT Filed: Nov. 28, 2014

(86) PCT No.: PCT/JP2014/081511
§ 371 (c)(1),
(2) Date: May 20, 2016

(87) PCT Pub. No.: WO2015/080241
PCT Pub. Date: Jun. 4, 2015

(65) Prior Publication Data
US 2016/0289237 A1 Oct. 6, 2016

(30) Foreign Application Priority Data

Nov. 29, 2013 (JP) .................... 2013-248201
Feb. 27, 2014 (JP) .................... 2014-037310

(51) Int. Cl.
*C08L 63/00* (2006.01)
*C07D 487/04* (2006.01)
(Continued)

(52) U.S. Cl.
CPC ......... *C07D 487/04* (2013.01); *C08G 59/245* (2013.01); *C08G 59/66* (2013.01);
(Continued)

(58) Field of Classification Search
CPC .... C08G 59/245; C08G 59/66; C08G 59/686; C07D 487/04; C08J 5/24; C08J 2363/00;
(Continued)

(56) References Cited

U.S. PATENT DOCUMENTS 4,721,814 A * 1/1988 Zahir .................... C07C 323/00
568/29
5,180,772 A 1/1993 Mao et al.
(Continued)

FOREIGN PATENT DOCUMENTS

EP 1 757 985 2/2007
JP 2-261851 10/1990
(Continued)

OTHER PUBLICATIONS

Miura et al., JP 11-171887 A machine translation in English, Jun. 29, 1999 (Year: 1999).*
(Continued)

*Primary Examiner* — David Thomas Karst
(74) *Attorney, Agent, or Firm* — Wenderoth, Lind & Ponack, L.L.P.

(57) ABSTRACT

The invention provides a mercaptoalkylglycoluril represented by the general formula (I):

(Continued)

wherein $R^1$ and $R^2$ each independently represent a hydrogen atom, a lower alkyl group, or a phenyl group; $R^3$, $R^4$, and $R^5$ each independently represent a hydrogen atom or a mercaptoalkyl group selected from a mercaptomethyl group, a 2-mercaptoethyl group, and a 3-mercaptopropyl group; and n is 0, 1, or 2. The invention further provides an epoxy resin composition comprising an epoxy resin and the mercaptoalkylglycoluril, and a method for producing a laminate or a multilayer printed circuit board using the same.

10 Claims, 5 Drawing Sheets

(51) Int. Cl.
| | |
|---|---|
| C08J 5/24 | (2006.01) |
| C08G 59/66 | (2006.01) |
| C08K 5/378 | (2006.01) |
| C09J 163/00 | (2006.01) |
| C23C 16/56 | (2006.01) |
| H05K 1/02 | (2006.01) |
| H05K 1/03 | (2006.01) |
| H05K 1/09 | (2006.01) |
| H05K 3/00 | (2006.01) |
| H05K 3/18 | (2006.01) |
| H05K 3/46 | (2006.01) |
| C08G 59/24 | (2006.01) |
| C08G 59/68 | (2006.01) |

(52) U.S. Cl.
CPC .............. *C08G 59/686* (2013.01); *C08J 5/24* (2013.01); *C08K 5/378* (2013.01); *C08L 63/00* (2013.01); *C09J 163/00* (2013.01); *C23C 16/56* (2013.01); *H05K 1/0298* (2013.01); *H05K 1/0353* (2013.01); *H05K 1/09* (2013.01); *H05K 3/0017* (2013.01); *H05K 3/18* (2013.01); *H05K 3/4655* (2013.01); *C08J 2363/00* (2013.01)

(58) Field of Classification Search
CPC ......... C08L 63/00; C08K 5/378; C23C 16/56; H05K 1/0298; H05K 1/0353; H05K 3/0017; H05K 3/18; H05K 3/4655; H05K 1/09; C09J 163/00
USPC .................................................. 525/528, 523
See application file for complete search history.

(56) References Cited

U.S. PATENT DOCUMENTS

| | | | |
|---|---|---|---|
| 5,430,112 A | 7/1995 | Sakata et al. | |
| 6,133,377 A | 10/2000 | Nakamura et al. | |

FOREIGN PATENT DOCUMENTS

| | | |
|---|---|---|
| JP | 6-211969 | 8/1994 |
| JP | 8-64960 | 3/1996 |
| JP | 11-1547 | 1/1999 |
| JP | 11-171887 | 6/1999 |
| JP | 2007-224167 | 9/2007 |
| JP | 2010-70634 | 4/2010 |

OTHER PUBLICATIONS

International Search Report dated Jan. 6, 2015 in International Application No. PCT/JP2014/081511.
STN International (Registry File), Oct. 3, 2013, [retrieved on Dec. 11, 2014] RN. 1454838-81-3 [online].
STN International (Registry File), Mar. 17, 2014, [retrieved on Dec. 11, 2014] RN. 1569262-17-4 [online].

* cited by examiner

MERCAPTOALKYLGLYCOLURILS AND USE OF SAME

TECHNICAL FIELD

The present invention relates to novel mercaptoalkylglycolurils and use of the same, particularly to use of the mercaptoalkylglycolurils as a curing agent for an epoxy resin, an epoxy resin composition containing the mercaptoalkylglycoluril, and use of such an epoxy resin composition.

One of the uses of the epoxy resin composition according to the present invention relates to an adhesive and a sealing agent containing the epoxy resin composition.

The epoxy resin composition is suitable for use as an interlayer insulating material as it has not only a high heat resistance but also a surface easily roughened with an oxidant. Thus, another use of the epoxy resin composition according to the invention relates to an adhesive film and a prepreg obtained by using the epoxy resin composition; a laminate and a multilayer printed circuit board obtained by using them; and a method for producing the laminate or the multilayer printed circuit board, particularly a method of producing the multilayer printed circuit board by a build-up method in which a conductor circuit layer and an insulating layer are alternatively stacked.

BACKGROUND ART

Glycolurils are heterocyclic compounds having four urea nitrogen atoms in the ring structure thereof, and are used in various applications and productions of novel functional compounds, utilizing the reactivity of the urea nitrogen.

It is known, for example, that the glycoluril is reacted with an aldehyde such as dimethoxyethanal to produce an aminoplastic resin, and the obtained resin is used as a cross-linking agent for cellulose (see Patent Document 1).

It is also known that an emulsion comprising a copolymer of vinyl acetate, ethylene, and a self-crosslinkable monomer, and a tetramethylol glycoluril is used as a binder for a non-woven fabric (see Patent Document 2). It is further known to use the tetramethylol glycoluril as a cross-linking agent for fixing a polyhexamethylene biguanide compound, which is a water-soluble polymer antimicrobial agent to a fiber (see Patent Document 3).

Meanwhile, compounds having plural allyl groups rich in reactivity in the molecule, such as triallylisocyanurates, are well-known as a cross-linking agent for synthetic resins and synthetic rubber. Similarly, tetraallyl-glycolurils having four allyl groups in the molecule, which function as a cross-linking agent for synthetic resins and synthetic rubber, are also known (see Patent Document 4).

Also, compounds having plural thiol groups in the molecule are well-known, for example, as a curing agent for an epoxy resin. For example, an epoxy resin composition comprising a polythiol compound as a curing agent and a reaction product of an amine with an epoxy compound as a curing accelerator is proposed. It is said that the epoxy resin composition has a long pot life and is quickly cured at a comparatively low temperature (see Patent Document 5).

An epoxy resin composition comprising, as a curing accelerator, a reaction product of an isocyanate compound having one or more isocyanate groups in the molecule with a compound having at least one primary and/or secondary amino group in the molecule is also proposed. It is said that the epoxy resin composition also has a long pot life and is superior in curability (see Patent Document 6).

Tris(3-mercaptopropyl)isocyanurate, which is also called "trithiol isocyanurate," has no ester group in the molecule. Thus, the use thereof as a curing agent capable of providing a cured product of epoxy resin superior in water resistance is proposed (see Patent Document 7).

A compound in which a hydrogen atom on at least one nitrogen atom of the glycoluril is replaced by a mercaptoalkyl group is useful, for example, as an intermediate for synthesizing a novel sulfur-containing compound or the like, and as a modifier such as a diluent for an epoxy resin or a plasticity-imparting agent, and it is expected to be useful as a curing agent for an epoxy resin. The compound in which a hydrogen atom on at least one nitrogen atom of the glycoluril is replaced by a mercaptoalkyl group, however, is still remains unknown.

Meanwhile, one of the important uses of the epoxy resin composition is use in a multilayer printed circuit board. Recently, as a method for producing a multilayer printed circuit board, a production technology of a build-up method in which a conductor layer on an inner layer circuit board and an organic insulating layer are alternatively stacked is receiving attention. For example, there is proposed a method for producing a multilayer printed circuit board comprising the steps of: coating a circuit-formed inner layer circuit board with an epoxy resin composition, curing it by heating, forming a roughened surface using a roughening agent, and forming a conductor layer on the roughened surface by plating (see Patent Documents 8 and 9).

A method for producing a multilayer printed circuit board is also disclosed which comprises the steps of: coating an inner layer circuit board with a primer adhesive, temporarily drying it, pasting it to a film-like additive adhesive, heating and curing it, roughening it with an alkaline oxidant, and forming a conductor layer by plating (see Patent Document 10).

An amine curing agent such as a dicyandiamide or imidazole compound is typically used as a curing agent in the epoxy resin composition used in the use described above. However, with the increase of a packaging density which has been recently advanced, a curing system superior in heat resistance to that of conventional system has also been desired in the interlayer insulating material used in the build-up method, similar to laminates.

Then, an epoxy resin composition for an interlayer insulating material is proposed which uses a phenol curing agent having a triazine structure and has both high heat resistance and surface-roughened property by an oxidant (see Patent Document 11).

The epoxy resin composition, however, contains a roughening component such as a rubber component as a requisite component, and thus the heat resistance and electric insulation thereof may sometimes be an issue in a field requiring more fine-patterning or thinner thickness of the insulating layer. When a phosphorus atom-containing epoxy resin, which is receiving attention as a flame-retardant epoxy resin from recent environmental issues, is used instead of a bromine-containing epoxy resin, a satisfactorily roughened surface cannot be obtained from an existing resin composition, and a conductor layer which is subsequently obtained by plating problematically has a weak peel strength.

CITATION LIST

Patent Literatures

Patent Document 1: JP-A No. H08-67729
Patent Document 2: JP-A No. H02-261851

Patent Document 3: JP-A No. H07-82665
Patent Document 4: JP-A No. H11-171887
Patent Document 5: JP-A No. H06-211969
Patent Document 6: JP-A No. H06-211970
Patent Document 7: JP-A No. 2012-153794
Patent Document 8: JP-A No. H07-304931
Patent Document 9: JP-A No. H07-304933
Patent Document 10: JP-A No. H08-64960
Patent Document 11: JP-A No. H11-1547

SUMMARY OF INVENTION

Technical Problem

In view of the circumstances described above, it is an object of the invention to provide novel mercaptoalkylglycolurils and use of the same, particularly use as a modifier, such as a diluent or a plasticity-imparting agent, and a curing agent for an epoxy resin, an epoxy resin composition comprising the mercaptoalkylglycoluril, and an adhesive and a sealing agent containing such an epoxy resin composition.

In particular, it is an object of the invention to provide an epoxy resin composition which comprises the mercaptoalkylglycoluril and provides a cured product superior in heat resistance and adhesion with a plated conductor layer, as the use of the epoxy resin composition.

It is a further object of the invention to provide an adhesive film, a prepreg, a laminate, and a multilayer printed circuit board obtained by using the epoxy resin composition which provides the cured product superior in heat resistance and adhesion with a plated conductor layer; and a method for producing the laminate or the multilayer printed circuit board.

Solution to Problem

The invention provides a mercaptoalkylglycoluril represented by the general formula (I):

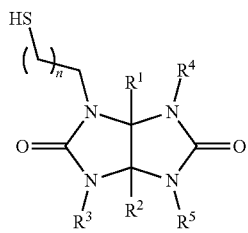

(I)

wherein $R^1$ and $R^2$ each independently represent a hydrogen atom, a lower alkyl group, or a phenyl group; $R^3$, $R^4$, and $R^5$ each independently represent a hydrogen atom or a mercaptoalkyl group selected from a mercaptomethyl group, a 2-mercaptoethyl group, and a 3-mercaptopropyl group; and n is 0, 1, or 2.

The invention provides a curing agent for an epoxy resin comprising the mercaptoalkylglycoluril as use of the same.

The invention also provides an epoxy resin composition comprising an epoxy resin and the mercaptoalkylglycoluril as use of the same.

Further, the invention provides an epoxy resin composition comprising an epoxy resin, the mercaptoalkylglycoluril, and a curing accelerator.

According to the invention, as the curing accelerator, one or more compounds from among amines, reaction products of the amine with an epoxy compound, and reaction products of an isocyanate compound having one or more isocyanate groups in the molecule with a compound having at least one primary and/or secondary amino group in the molecule are preferably used.

In addition to the above, the invention provides an adhesive and a sealing agent comprising the epoxy resin composition.

Further according to the invention, as the epoxy resin has a property capable of providing a cured product superior in heat resistance and adhesion with a plated conductor, the following uses are provided as the use of the epoxy resin composition.

(1) An adhesive film comprising a support base film and a thin film of the epoxy resin composition formed on the support base film;

(2) A prepreg comprising a sheet-shaped reinforcement substrate formed from a fiber, wherein the sheet-shaped reinforcement substrate is impregnated with a semi-cured product formed from the epoxy resin composition;

(3) A multilayer printed circuit board comprising a cured layer of the epoxy resin composition, a plated conductor layer formed on one roughened surface of the cured layer of the epoxy resin, and a pattern-processed inner layer circuit board laminated closely to the other surface of the cured layer of the epoxy resin;

(4) A multilayer printed circuit board obtained by coating a pattern-processed inner layer circuit board with the epoxy resin composition, curing the epoxy resin composition by heating, roughening a surface of the obtained cured product with an oxidant, and forming a conductor layer on the roughened surface;

(5) A multilayer printed circuit board obtained by laminating the adhesive film on a pattern-processed inner layer circuit board with pressurizing and heating, curing the epoxy resin composition by heating while the support base film is peeled off or is not peeled off, roughening a surface of the obtained cured product with an oxidant, and forming a conductor layer on the roughened surface by plating;

(6) A multilayer printed circuit board obtained by laminating and integrating the prepreg on a pattern-processed inner layer circuit board with pressurizing and heating, roughening a surface of the prepreg with an oxidant, and forming a conductor layer on the roughened surface by plating;

(7) A method for producing a multilayer printed circuit board comprising the steps of: coating a pattern-processed inner layer circuit board with the epoxy resin composition; curing the epoxy resin composition by heating; roughening a surface of the obtained cured product with an oxidant; and forming a conductor layer on the roughened surface by plating;

(8) A method for producing a multilayer printed circuit board comprising the steps of: laminating the adhesive film on a pattern-processed inner layer circuit board with pressurizing and heating; curing the epoxy resin composition by heating while the support base film is peeled off or is not peeled off; roughening a surface of the obtained cured product with an oxidant; and forming a conductor layer on the roughened surface by plating;

(9) A method for producing a multilayer printed circuit board comprising the steps of: laminating and integrating the prepreg on a pattern-processed inner layer circuit board with pressurizing and heating; roughening a surface of the prepreg with an oxidant; and forming a conductor layer on the roughened surface by plating;

(10) A laminate obtained by coating a surface of a both-face copper clad laminate from which a copper foil is etched out or at least one surface of an unclad plate with the epoxy resin composition, and curing it by heating.

(11) A laminate obtained by laminating the adhesive film on a surface of a both-face copper clad laminate from which a copper foil is etched out or at least one surface of an unclad plate with pressurizing and heating, if necessary, peeling off the support base film, and curing it by heating;
(12) A laminate obtained by laminating the prepreg on a surface of a both-face copper clad laminate from which a copper foil is etched out or at least one surface of an unclad plate with pressurizing and heating; and
(13) A laminate obtained by laminating the prepregs with pressurizing and heating.

Advantageous Effects of Invention

The mercaptoalkylglycolurils according to the invention are novel compounds in which at least one hydrogen atom of hydrogen atoms on four nitrogen atoms present in glycolurils is replaced by a mercaptoalkyl group.

Such a compound, accordingly, is useful as an intermediate for synthesizing a novel sulfur-containing compound and, as described above, is also useful as a modifier or a curing agent for an epoxy resin utilizing the reactivity with an epoxy group.

In particular, according to the present invention, a compound having two or more mercaptoalkyl groups in the molecule is preferably useful, for example, as a curing agent for an epoxy resin. For example, 1,3,4,6-tetrakis(mercaptoalkyl)glycolurils are tetrafunctional, and thus provide a cured product of epoxy resin having a higher cross-linking density, i.e., a cured product of epoxy resin far superior, for example, in hardness, heat resistance, and moisture resistance, as compared with a case where a conventional bifunctional or trifunctional curing agent is used.

Also, the mercaptoalkylglycolurils according to the invention have no ester groups in the molecule, and thus provide a cured product of epoxy resin having a far superior hydrolysis resistance to that obtained in a case of using conventional polythiols. As a result, there is obtained therefrom an adhesive and a sealing agent which comprises the mercaptoalkylglycoluril according to the invention, and is superior in strength, heat resistance, and moisture resistance.

Further, the epoxy resin composition comprising the mercaptoalkylglycoluril according to the invention provides a cured product superior in heat resistance and adhesion with a plated conductor layer, and thus the epoxy resin composition of the invention can be preferably used, for example, in production of a laminate or a multilayer printed circuit board.

DESCRIPTION OF EMBODIMENTS (Mercaptoalkylglycolurils)

Figure 1:
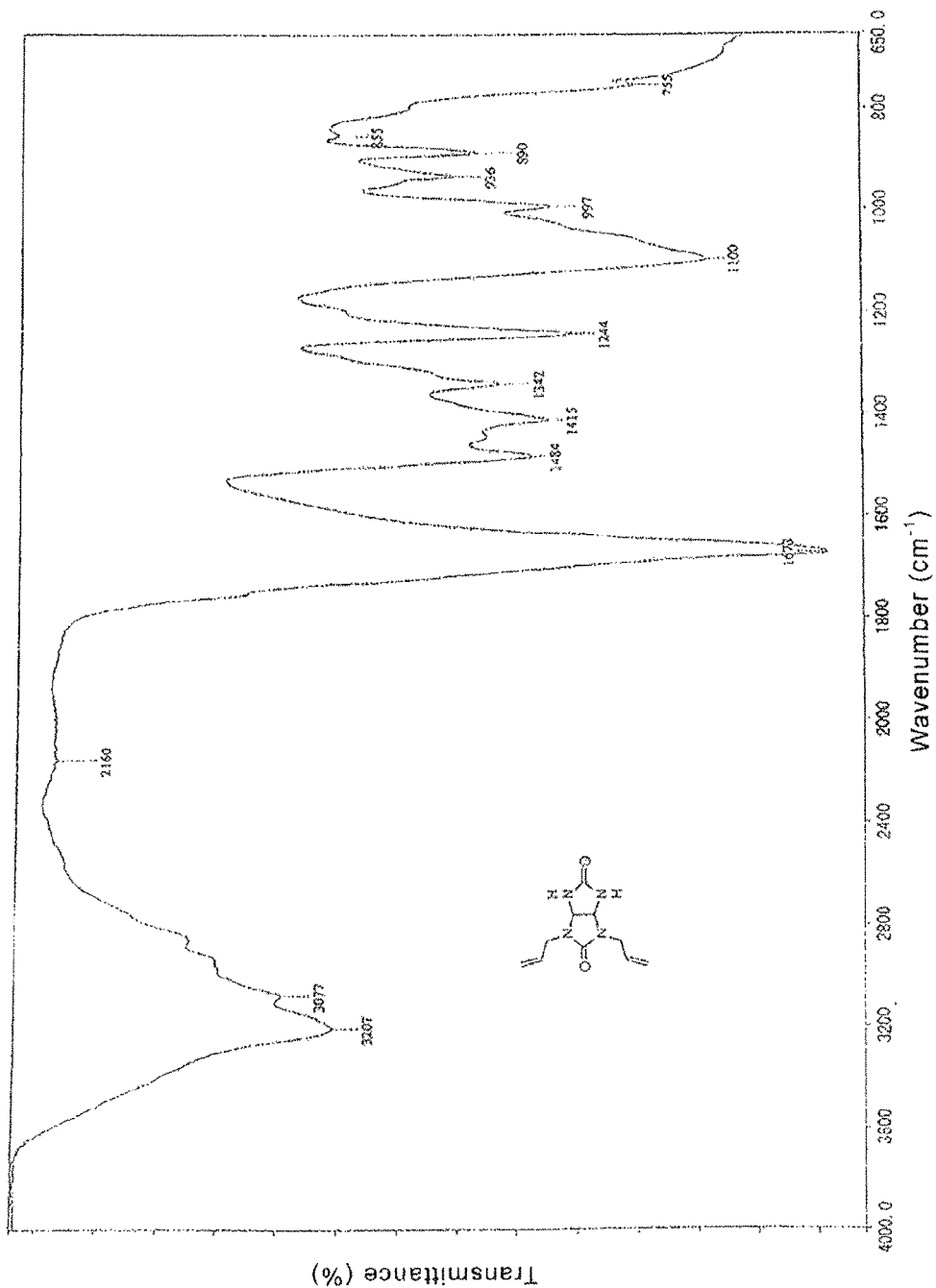
FIG. 1 shows IR spectrum of 1,3-diallylglycoluril.

The mercaptoalkylglycolurils of the invention are represented by the general formula (I):

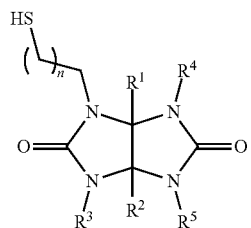

(I)

wherein $R^1$ and $R^2$ each independently represent a hydrogen atom, a lower alkyl group, or a phenyl group; $R^3$, $R^4$, and $R^5$ each independently represent a hydrogen atom or a mercaptoalkyl group selected from a mercaptomethyl group, a 2-mercaptoethyl group, and a 3-mercaptopropyl group; and n is 0, 1, or 2.

In the mercaptoalkylglycolurils represented by the general formula (I), when $R^1$ or $R^2$ is a lower alkyl group, the lower alkyl group has generally 1 to 5 carbon atoms, preferably 1 to 3 carbon atoms, and most preferably one carbon atom, i.e., the group is a methyl group.

The preferable mercaptoalkylglycolurils of the invention are represented by the general formula (I').

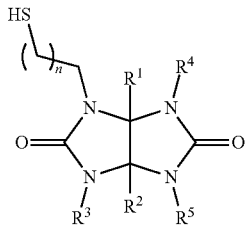

(I')

wherein $R^1$ and $R^2$ each independently represent a hydrogen atom, a lower alkyl group, or a phenyl group; $R^3$, $R^4$, and $R^5$ each independently represent a hydrogen atom or a mercaptoalkyl group which is the same as a part of the general formula (I'):

and n is 0, 1, or 2.

In the invention, in the mercaptoalkylglycolurils represented by the general formula (I'), when one, two, or three of $R^3$, $R^4$, and $R^5$ are mercaptoalkyl groups, it is preferable that the mercaptoalkyl groups present in the mercaptoalkylglycoluril represented by the general formula (I') are all the same.

Preferable examples of the mercaptoalkylglycoluril according to the invention, accordingly, may include:
1-mercaptomethyl glycoluril,
1-(2-mercaptoethyl)glycoluril,
1-(3-mercaptopropyl)glycoluril,
1,3-bis(mercaptomethyl)glycoluril,
1,3-bis(2-mercaptoethyl)glycoluril,
1,3-bis(3-mercaptopropyl)glycoluril,
1,4-bis(mercaptomethyl)glycoluril,
1,4-bis(2-mercaptoethyl)glycoluril,
1,4-bis(3-mercaptopropyl)glycoluril,
1,6-bis(mercaptomethyl)glycoluril, 1,6-bis(2-mercaptoethyl)glycoluril,
1,6-bis(3-mercaptopropyl)glycoluril,
1,3,4-tris(mercaptomethyl)glycoluril,
1,3,4-tris(2-mercaptoethyl)glycoluril,
1,3,4-tris(3-mercaptopropyl)glycoluril,
1,3,4,6-tetrakis(mercaptomethyl)glycoluril,
1,3,4,6-tetrakis(2-mercaptoethyl)glycoluril,
1,3,4,6-tetrakis(3-mercaptopropyl)glycoluril,
1-mercaptomethyl-3a-methylglycoluril,
1-mercaptomethyl-6a-methylglycoluril,
1-(2-mercaptoethyl)-3a-methylglycoluril,
1-(2-mercaptoethyl)-6a-methylglycoluril,
1-(3-mercaptopropyl)-3a-methylglycoluril,
1-(3-mercaptopropyl)-6a-methylglycoluril,
1,3-bis(mercaptomethyl)-3a-methylglycoluril,
1,3-bis(2-mercaptoethyl)-3a-methylglycoluril,
1,3-bis(3-mercaptopropyl)-3a-methylglycoluril,
1,4-bis(mercaptomethyl)-3a-methylglycoluril,
1,4-bis(2-mercaptoethyl)-3a-methylglycoluril,
1,4-bis(3-mercaptopropyl)-3a-methylglycoluril,
1,6-bis(mercaptomethyl)-3a-methylglycoluril,
1,6-bis(mercaptomethyl)-6a-methylglycoluril,
1,6-bis(2-mercaptoethyl)-3a-methylglycoluril,
1,6-bis(2-mercaptoethyl)-6a-methylglycoluril,
1,6-bis(3-mercaptopropyl)-3a-methylglycoluril,
1,6-bis(3-mercaptopropyl)-6a-methylglycoluril,
1,3,4-tris(mercaptomethyl)-3a-methylglycoluril,
1,3,4-tris(mercaptomethyl)-6a-methylglycoluril,
1,3,4-tris(2-mercaptoethyl)-3a-methylglycoluril,
1,3,4-tris(2-mercaptoethyl)-6a-methylglycoluril,
1,3,4-tris(3-mercaptopropyl)-3a-methylglycoluril,
1,3,4-tris(3-mercaptopropyl)-6a-methylglycoluril,
1,3,4,6-tetrakis(mercaptomethyl)-3a-methylglycoluril,
1,3,4,6-tetrakis(2-mercaptoethyl)-3a-methylglycoluril,
1,3,4,6-tetrakis(3-mercaptopropyl)-3a-methylglycoluril,
1-mercaptomethyl-3a,6a-dimethylglycoluril,
1-(2-mercaptoethyl)-3a,6a-dimethylglycoluril,
1-(3-mercaptopropyl)-3a,6a-dimethylglycoluril,
1,3-bis(mercaptomethyl)-3a,6a-dimethylglycoluril,
1,3-bis(2-mercaptoethyl)-3a,6a-dimethylglycoluril,
1,3-bis(3-mercaptopropyl)-3a,6a-dimethylglycoluril,
1,4-bis(mercaptomethyl)-3a,6a-dimethylglycoluril,
1,4-bis(2-mercaptoethyl)-3a,6a-dimethylglycoluril,
1,4-bis(3-mercaptopropyl)-3a,6a-dimethylglycoluril,
1,6-bis(mercaptomethyl)-3a,6a-dimethylglycoluril,
1,6-bis(2-mercaptocthyl)-3a,6a-dimethylglycoluril,
1,6-bis(3-mercaptopropyl)-3a,6a-dimethylglycoluril,
1,3,4-tris(mercaptomethyl)-3a,6a-dimethylglycoluril,
1,3,4-tris(2-mercaptoethyl)-3a,6a-dimethylglycoluril,
1,3,4-tris(3-mercaptopropyl)-3a,6a-dimethylglycoluril,
1,3,4,6-tetrakis(mercaptomethyl)-3a,6a-dimethylglycoluril,
1,3,4,6-tetrakis(2-mercaptoethyl)-3a,6a-dimethylglycoluril,
1,3,4,6-tetrakis(3-mercaptopropyl)-3a,6a-dimethylglycoluril,
1-mercaptomethyl-3a,6a-diphenylglycoluril,
1-(2-mercaptoethyl)-3a,6a-diphenylglycoluril,
1-(3-mercaptopropyl)-3a,6a-diphenylglycoluril,
1,3-bis(mercaptomethyl)-3a,6a-diphenylglycoluril,
1,3-bis(2-mercaptoethyl)-3a,6a-diphenylglycoluril,
1,3-bis(3-mercaptopropyl)-3a,6a-diphenylglycoluril,
1,4-bis(mercaptomethyl)-3a,6a-diphenylglycoluril,
1,4-bis(2-mercaptoethyl)-3a,6a-diphenylglycoluril,
1,4-bis(3-mercaptopropyl)-3a,6a-diphenylglycoluril,
1,6-bis(mercaptomethyl)-3a,6a-diphenylglycoluril,
1,6-bis(2-mercaptoethyl)-3a,6a-diphenylglycoluril,
1,6-bis(3-mercaptopropyl)-3a,6a-diphenylglycoluril,
1,3,4-tris(mercaptomethyl)-3a,6a-diphenylglycoluril,
1,3,4-tris(2-mercaptoethyl)-3a,6a-diphenylglycoluril,
1,3,4-tris(3-mercaptopropyl)-3a,6a-diphenylglycoluril,
1,3,4,6-tetrakis(mercaptomethyl)-3a,6a-diphenylglycoluril,
1,3,4,6-tetrakis(2-mercaptoethyl)-3a,6a-diphenylglycoluril,
1,3,4,6-tetrakis(3-mercaptopropyl)-3a,6a-diphenylglycoluril, and the like.

Among the mercaptoalkylglycolurils represented by the general formula (I) according to the invention, mercaptoalkylglycolurils wherein n is 2, i.e., 3-mercaptopropylglycolurils represented by the general formula (Ia):

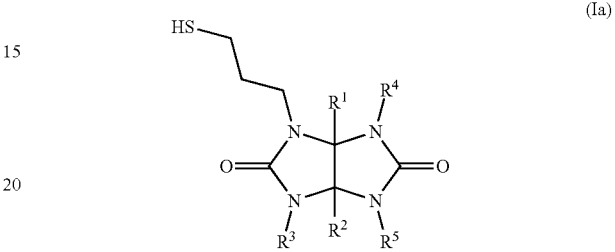

wherein $R^1$ and $R^2$ are the same as above, and $R^3$, $R^4$, and $R^5$ each independently represent a hydrogen atom or a 3-mercaptopropyl group can be obtained by addition-reaction of thioacetic acid with an allylglycoluril represented by the general formula (a):

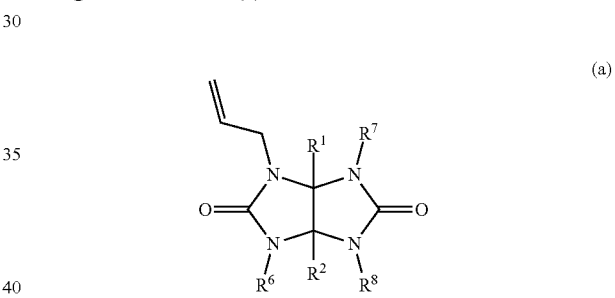

wherein $R^1$ and $R^2$ are the same as above, and $R^6$, $R^7$, and $R^8$ each independently represent a hydrogen atom or an allyl group, if necessary in an appropriate solvent, in the presence of a catalyst to obtain a thioacetic acid ester represented by the general formula (a1):

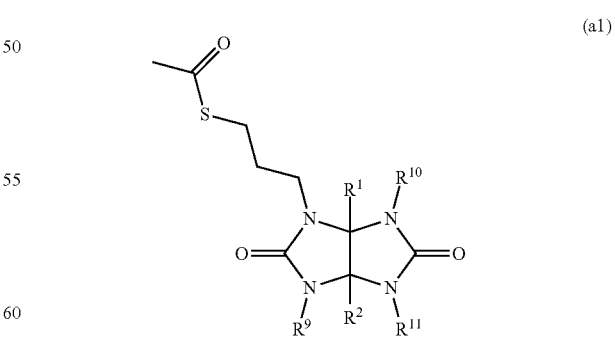

wherein $R^1$ and $R^2$ are the same as above, and $R^9$, $R^{10}$, and $R^{11}$ each independently represent a hydrogen atom or a 3-acetylthiopropyl group as a reaction product; and then reducing the reaction product, if necessary in an appropriate solvent, with a borohydride compound.

In the reaction of the allylglycoluril (a) with the thioacetic acid, the thioacetic acid is used in a ratio of generally 1.0 to 3.0 equivalents, preferably 1.0 to 1.5 equivalents to the allyl group in the allylglycoluril (a).

The reaction of the allylglycoluril (a) with the thioacetic acid is performed in the presence of the catalyst. Azobisisobutyronitrile or benzoyl peroxide is preferably used as the catalyst. The catalyst is used in a ratio of 0.001 to 0.2 equivalents, preferably 0.005 to 0.2 equivalents to the allyl group in the allylglycoluril (a).

In the reaction of the allyl glycoluril (a) with the thioacetic acid, when the solvent is used, it is not particularly limited so long as it does not hinder the reaction. Examples of the solvent may include: water; alcohols such as methanol, ethanol, and isopropyl alcohol; aliphatic hydrocarbons such as hexane and heptane; ketones such as acetone and 2-butanone; esters such as ethyl acetate and butyl acetate; aromatic hydrocarbons such as benzene, toluene, and xylene; halogenated hydrocarbons such as methylene chloride, chloroform, carbon tetrachloride, chlorotrifluoromethane, dichloroethane, chlorobenzene, and dichlorobenzene; ethers such as diethyl ether, diisopropyl ether, tetrahydrofuran, dioxane, dimethoxyethane, and diethyleneglycol dimethyl ether; amides such as formamide, N,N-dimethylformamide, N,N-dimethylacetamide, N-methyl-2-pyrrolidone, and hexamethylphosphorotriamide; sulfoxides such as dimethyl sulfoxide; and the like. The solvents are used alone or as a mixture of two or more kinds.

The reaction of the allyl glycoluril (a) with the thioacetic acid is performed generally at a temperature within a range of −10 to 150° C., preferably a temperature within a range of 0° C. to 100° C. The reaction time depends on the reaction temperature, and it is generally within a range of 1 to 48 hours, preferably 1 to 24 hours.

After the reaction of the allylglycoluril (a) with the thioacetic acid is finished, excessive thioacetic acid and solvent are distilled away from the obtained reaction mixture, and then the reaction product, which is obtained as a residue, may be reduced with the borohydride compound, if necessary in the appropriate solvent, or the obtained reaction mixture may be subjected to the reduction treatment with the borohydride compound, if necessary in the appropriate solvent, as it is.

As the borohydride compound, for example, sodium borohydride, potassium borohydride, lithium borohydride, calcium borohydride, magnesium borohydride, or the like is used. The borohydride compound is used in a ratio of 0.5 to 10 equivalents, preferably 1.0 to 4.0 equivalents to the allyl group in the allylglycoluril used.

In the reduction treatment of the reaction product obtained by the reaction of the allylglycoluril (a) with the thioacetic acid using the borohydride compound, when the solvent is used, it is not particularly limited so long as it does not hinder the reaction. For example, the same solvents as those used in the reaction of the allylglycoluril (a) with the thioacetic acid may be used.

The reduction treatment with the borohydride compound is performed generally at a temperature within a range of 0° C. to 150° C., preferably at a temperature within a range of room temperature to 100° C. The reaction time depends on the reaction temperature, and it is generally within a range of 1 to 24 hours, preferably 1 to 12 hours.

After the reduction treatment with the borohydride compound, the desired mercaptoalkylglycoluril can be obtained from the obtained reaction mixture, for example, by an extract operation. If necessary, the desired mercaptoalkylglycoluril may be purified by washing with a solvent such as water, an activated carbon treatment, or the like.

Among the mercaptoalkylglycolurils represented by the general formula (I) according to the invention, mercaptoalkylglycolurils wherein n is 1, i.e., 2-ethylmercaptoglycolurils represented by the general formula (Ib):

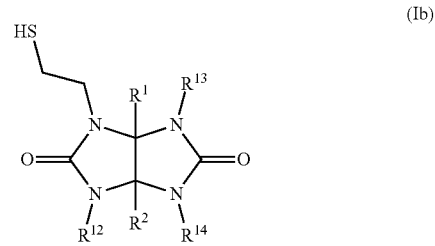

wherein $R^1$ and $R^2$ are the same as above, and $R^{12}$, $R^{13}$, and $R^{14}$ each independently represent a hydrogen atom or a 2-mercaptoethyl group can be obtained by reacting thionyl chloride with a 2-hydroxyethylglycoluril (b) represented by the general formula (b)

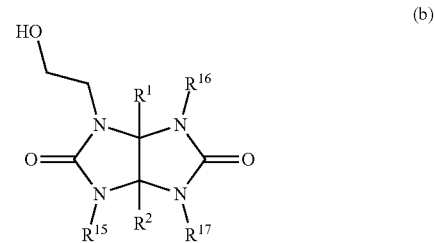

wherein $R^1$ and $R^2$ are the same as above, and $R^{15}$, $R^{16}$, and $R^{17}$ each independently represent a hydrogen atom or a 2-hydroxyemethyl group, if necessary in an appropriate solvent, to obtain a reaction product represented by the general formula (b1):

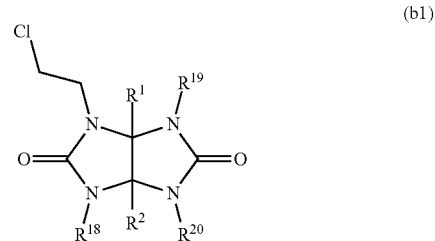

wherein $R^1$ and $R^2$ are the same as above, and $R^{18}$, $R^{19}$, and $R^{20}$ each independently represent a hydrogen atom or a 2-chloroethyl group, i.e., a 2-chloroethylglycoluril; and then treating the reaction product with disodium trithiocarbonate, if necessary in an appropriate solvent, and substituting the chlorine atoms by mercapto groups.

Similarly, among the mercaptoalkylglycolurils represented by the general formula (I) according to the invention, mercaptoalkylglycolurils wherein n is 0, i.e., mercaptomethylglycolurils represented by the general formula (Ic):

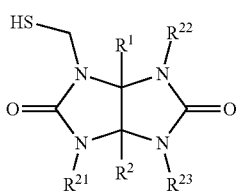

(Ic)

wherein $R^1$ and $R^2$ are the same as above, and $R^{21}$, $R^{22}$, and $R^{23}$ each independently represent a hydrogen atom or a mercaptomethyl group can be obtained in the same manner as in the 2-ethylmercaptoglycolurils.

The mercaptomethylglycolurils can be obtained by reacting thionyl chloride with a hydroxymethylglycoluril (c) represented by the general formula (c):

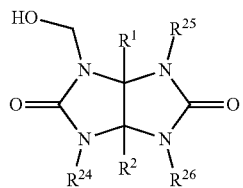

(c)

wherein $R^1$ and $R^2$ are the same as above, and $R^{24}$, $R^{25}$, and $R^{26}$ each independently represent a hydrogen atom or a hydroxymethyl group, if necessary in an appropriate solvent to obtain a reaction product represented by the general formula (c1):

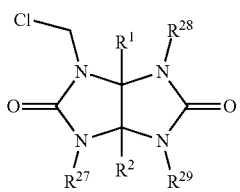

(c1)

wherein $R^1$ and $R^2$ are the same as above, and $R^{27}$, $R^{28}$, and $R^{29}$ each independently represent a hydrogen atom or a chloromethyl group, i.e., a chloromethylglycoluril; and then treating the reaction product with and with disodium trithiocarbonate, if necessary in an appropriate solvent, and substituting the chlorine atoms by mercapto groups.

In the reaction of the 2-hydroxyethylglycoluril (b) or the hydroxymethylglycoluril (c) with thionyl chloride, thionyl chloride is used in a ratio of generally 1.0 to 10.0 equivalents, preferably 1.0 to 3.0 equivalents to the hydroxyl group in the 2-hydroxyethylglycoluril (b) or the hydroxymethylglycoluril (c).

In the reaction of the 2-hydroxyethylglycoluril (b) or the hydroxymethylglycoluril (c) with the thionyl chloride, when the solvent is used, it is not particularly limited so long as it does not hinder the reaction. Examples of the solvent may include: aliphatic hydrocarbons such as hexane and heptane; ketones such as acetone and 2-butanone; esters such as ethyl acetate and butyl acetate; aromatic hydrocarbons such as benzene, toluene, and xylene; halogenated hydrocarbons such as methylene chloride, chloroform, carbon tetrachloride, chlorotrifluoromethane, dichloroethane, chlorobenzene, and dichlorobenzene; ethers such as diethyl ether, diisopropyl ether, tetrahydrofuran, dioxane, dimethoxyethane, and diethyleneglycol dimethyl ether; amides such as formamide, N,N-dimethylformamide, N,N-dimethylacetamide, N-methyl-2-pyrrolidone, and hexamethylphosphorotriamide; sulfoxides such as dimethyl sulfoxide; and the like. The solvents are used alone or as a mixture of two or more kinds.

The reaction of the 2-hydroxyethylglycoluril (b) or the hydroxymethylglycoluril (c) with the thionyl chloride is performed generally at a temperature within a range of −10 to 150° C., preferably a temperature within a range of 0° C. to 100° C. The reaction time depends on the reaction temperature, and it is generally within a range of 1 to 24 hours, preferably 1 to 6 hours.

After the reaction of the 2-hydroxyethylglycoluril (b) or the hydroxymethylglycoluril (c) with the thionyl chloride, excessive thionyl chloride and solvent are distilled away from the obtained reaction mixture, and then the reaction product, which is obtained as a residue, may be treated with disodium trithiocarbonate, if necessary in the appropriate solvent, or after the reaction of the 2-hydroxyethylglycoluril (b) or the hydroxymethylglycoluril (c) with the thionyl chloride, the obtained reaction mixture is treated with disodium trithiocarbonate, if necessary in the appropriate solvent, as it is.

The disodium trithiocarbonate is used in a ratio of 1.0 to 10 equivalents, preferably 1.0 to 4.0 equivalents to the hydroxyl group in the 2-hydroxyethylglycoluril (b) or hydroxymethylglycoluril (c) used.

In the treatment of the reaction product obtained by the reaction of the 2-hydroxyethylglycoluril (b) or the hydroxymethylglycoluril (c) with the thionyl chloride, with the disodium trithiocarbonate, when the solvent is used, it is not particularly limited so long as it does not hinder the reaction. For example, the same solvents as those used in the reaction of the allylglycoluril (a) with the thioacetic acid may be used.

The treatment with the disodium trithiocarbonate is performed generally at a temperature within a range of 0° C. to 150° C., preferably a temperature within a range of room temperature to 100° C. The reaction time depends on the reaction temperature, and it is generally within a range of 1 to 24 hours, preferably 1 to 9 hours.

After the treatment with the disodium trithiocarbonate is finished, the desired mercaptoalkylglycoluril can be obtained from the treated mixture, for example, by an extract operation. If necessary, the desired mercaptoalkylglycoluril may be purified by washing with a solvent such as water, an activated carbon treatment, or the like.

The mercaptoalkylglycolurils according to the invention as described above are useful as a synthetic intermediate of a novel sulfur-containing compound. In addition, they have reactivity with an epoxy group, and thus they are useful as a modifier such as a diluent or a plasticity-imparting agent or a curing agent for the epoxy resin.

(Epoxy Resin Composition)

Epoxy resin compositions comprising the mercaptoalkylglycoluril of the invention are explained below.

The epoxy resin composition according to the invention comprises the mercaptoalkylglycoluril represented by the general formula (I) and, preferably a curing accelerator.

As the curing accelerator, curing accelerators comprising an amine, curing accelerators comprising a reaction product of an amine with an epoxy compound, curing accelerators comprising a reaction product of a compound having one or more isocyanate groups in the molecule with a compound having at least one primary and/or secondary amino group in the molecule, and the like are used. The curing accelerators are used alone or as a mixture of two or more kinds.

The epoxy resin composition according to the invention preferably comprises a mercaptoalkylglycoluril having two or more mercaptoalkyl group in the molecule, i.e., among the mercaptoalkylglycolurils represented by the general formula (I), the mercaptoalkylglycolurils having two or more mercaptoalkyl groups in the molecule, as a curing agent, and more preferably further comprises a curing accelerator.

In particular, according to the invention, as an example, an epoxy resin composition comprising 1,3,4,6-tetrakis(mercaptoalkyl)glycoluril as the curing agent provides a cured product of epoxy resin which has not only a superior hydrolysis resistance, but also a higher cross-linking density and thus has, for example, far superior hardness, heat resistance, and moisture resistance, and moreover a superior adhesion with a plated conductor layer, as compared with a conventionally known epoxy resin composition.

In the epoxy resin composition of the invention, the mercaptoalkylglycoluril of the invention is used so that a ratio of SH equivalent number/epoxy equivalent number is within a range of 0.1 to 3.0, preferably 0.5 to 2.0, most preferably 0.5 to 1.2.

Although the epoxy resin refers to generally a low molecular weight prepolymer having two or more epoxy groups in one molecule on an average, as typically exemplified by such a polyglycidyl ether that is obtained by reaction of bisphenol A with epichlorohydrin, the epoxy resin in the present invention refers to an epoxy compound having two or more epoxy groups in the molecule on an average, and thus includes not only the low molecular weight prepolymer described above, but also monomer type epoxy compounds having two or more epoxy groups in the molecule.

In the present invention, accordingly, as well known, examples of the epoxy resin may include: polyglycidyl ethers obtained by reacting a polyhydric phenol such as bisphenol A, bisphenol F, bisphenol S, bisphenol AD, catechol, or resorcinol, or polyhydric alcohol such as glycerol or polyethylene glycol with epichlorohydrin; glycidylether esters obtained by reacting a hydroxycarboxylic acid such as p-hydroxybenzoic acid or β-hydroxynaphthoic acid with epichlorohydrin; polyglycidyl esters obtained by reacting a polycarboxylic acid such as phthalic acid or terephthalic acid with epichlorohydrin; epoxy compounds of a condensate of phenol with an aromatic aldehyde having a phenolic hydroxyl group; epoxidized phenol novolak resins, epoxidized cresol novolak resins, epoxidized polyolefins, cyclic aliphatic epoxy resins, dicyclopentadiene-type epoxy resins, naphthalene-type epoxy resins, urethane-modified epoxy resins, and the like. In the present invention, however, the epoxy resins are not limited to the examples described above. The epoxy resin may include a monofunctional epoxy resin as a reactive diluent.

In the present invention, the epoxy resin may include a phosphorus atom. Also, a phosphorus atom-containing epoxy resin, which is receiving attention as a flame-retardant epoxy resin, may be used instead of an epoxy resin bromide. Examples of the phosphorus atom-containing epoxy resin may include those disclosed in JP-A No. H04-11662 and JP-A No. H11-166035.

As the epoxy resin, the glycidylglycoluril compound having two or more epoxy groups in the molecule may also be used. Examples of such a glycidylglycoluril compound may include:
1,3-diglycidylglycoluril,
1,4-diglycidylglycoluril,
1,6-diglycidylglycoluril,
1,3,4-triglycidylglycoluril,
1,3,4,6-tetraglycidylglycoluril,
1,3-diglycidyl-3a-methylglycoluril,
1,4-diglycidyl-3a-methylglycoluril,
1,6-diglycidyl-3a-methylglycoluril,
1,3,4-triglycidyl-3a-methylglycoluril,
1,3,4,6-tetraglycidyl-3a-methylglycoluril,
1,3-diglycidyl-3a,6a-dimethylglycoluril,
1,4-diglycidyl-3a,6a-dimethylglycoluril,
1,6-diglycidyl-3a,6a-dimethylglycoluril,
1,3,4-triglycidyl-3a,6a-dimethylglycoluril,
1,3,4,6-tetraglycidyl-3a,6a-dimethylglycoluril,
1,3-diglycidyl-3a,6a-diphenylglycoluril,
1,4-diglycidyl-3a,6a-diphenylglycoluril,
1,6-diglycidyl-3a,6a-diphenylglycoluril,
1,3,4-triglycidyl-3a,6a-diphenylglycoluril,
1,3,4,6-tetraglycidyl-3a,6a-diphenylglycoluril,
and the like.

Further, triglycidylisocyanurate having three epoxy groups in the molecule may also be used as the epoxy resin, similar to the glycidyl-glycolurils.

In the invention, the epoxy resins as described above may be used alone or as a mixture of two or more kinds.

The curing accelerator comprising the amine in the epoxy resin composition according to the invention is, as conventionally known, a compound which has one or more active hydrogen atoms which is addition-reactive with an epoxy group in the molecule, and has at least one amino group selected from a primary amino group, a secondary amino group, and a tertiary amino group in the molecule.

Examples of the curing accelerator comprising an amine may include: aliphatic amines such as diethylenetriamine, triethylenetetramine, n-propyl amine, 2-hydroxyethylaminopropylamine, cyclohexylamine, and 4,4'-diaminodicyclohexyl methane; aromatic amines such as 4,4'-diaminodiphenyl methane and o-methyl aniline; nitrogen-containing heterocyclic compounds such as 2-ethyl-4-methylimidazole, 2-methylimidazole, 2-ethyl-4-methylimidazoline, 2,4-dimethylimidazoline, piperidine, and piperazine; and the like.

In the present invention, however, the curing accelerators containing the amine are not limited to the examples described above. The various curing accelerators described above may be used alone or as a mixture of two or more kinds.

In the epoxy resin composition according to the present invention, in addition to the curing accelerator containing the amine described above, the reaction product of the amine with the epoxy compound, or the reaction product of the compound having one or more isocyanate groups in the molecule with the compound having at least one primary and/or secondary amino group in the molecule may also be used as the curing accelerator.

The reaction product of the amine with the epoxy compound is solid and insoluble in the epoxy resin at room temperature but is solubilized by heating to function as the curing accelerator, and thus it is also called as a "latent curing accelerator." Hereinafter, the curing accelerator comprising the reaction product of the amine with the epoxy compound is referred to as the "latent curing accelerator." The latent curing accelerator may be subjected to a surface treatment with an isocyanate compound or an acidic compound.

Examples of the epoxy compound used in the production of the latent curing accelerator may include, but are not limited to: polyglycidyl ethers obtained by reacting a polyhydric phenol such as bisphenol A, bisphenol F, catechol, or resorcinol, or a polyhydric alcohol such as glycerol or polyethylene glycol with epichlorohydrin; glycidyl ether esters obtained by reacting a hydroxycarboxylic acid such as p-hydroxybenzoic acid or β-hydroxynaphthoic acid with epichlorohydrin; polyglycidyl esters obtained by reacting a polycarboxylic acid such as phthalic acid or terephthalic acid with epichlorohydrin; glycidyl amine compounds obtained by reacting 4,4'-diaminodiphenyl methane or m-aminophenol with epichlorohydrin; polyfunctional epoxy compounds such as epoxidized phenol novolak resins, epoxidized cresol novolak resins, and epoxidized polyolefins; monofunctional epoxy compounds such as butyl glycidyl ether, phenyl glycidyl ether, and glycidyl methacrylate; and the like.

The amines used in the production of the latent curing accelerator may be compounds which have one or more active hydrogen atoms addition-reactive with the epoxy group in the molecule, and have at least one amino group selected from a primary amino group, a secondary amino group, and a tertiary amino group in the molecule.

Examples of the amines may include, but are not limited to: aliphatic amines such as diethylenetriamine, triethylenetetramine, n-propyl amine, 2-hydroxyethylaminopropylamine, cyclohexylamine, and 4,4'-diaminodicyclohexyl methane; aromatic amine compounds such as 4,4'-diaminodiphenyl methane and o-methyl aniline; nitrogen-containing heterocyclic compounds such as 2-ethyl-4-methylimidazole, 2-methylimidazole, 2-ethyl-4-methylimidazoline, 2,4-dimethylimidazoline, piperidine, and piperazine; and the like.

Of the amines described above, tertiary amines having a tertiary amino group in the molecule are starting materials capable of providing a latent curing accelerator superior in cure-accelerating property. Examples of the tertiary amines may include: amines such as dimethylaminopropylamine, diethylaminopropylamine, di-n-propylamino-propylamine, dibutylaminopropylamine, dimethylaminoethylamine, diethylamino-ethylamine, and N-methylpiperazine; primary or secondary amines having a tertiary amino group in the molecule such as imidazole compound, for example, 2-methylimidazole, 2-ethylimidazole, 2-ethyl-4-methylimidazole, and 2-phenylimidazole; alcohols, phenols, thiols, carboxylic acids, and hydrazides containing a tertiary amino group in the molecule, such as 2-dimethyl aminoethanol, 1-methyl-2-dimethyl aminoethanol, 1-phenoxymethyl-2-dimethyl aminoethanol, 2-diethyl aminoethanol, 1-butoxymethyl-2-dimethyl aminoethanol, 1-(2-hydroxy-3-phenoxypropyl)-2-methylimidazole, 1-(2-hydroxy-3-phenoxypropyl)-2-ethyl-4-methylimidazole, 1-(2-hydroxy-3-butoxypropyl)-2-methylimidazole, 1-(2-hydroxy-3-butoxypropyl)-2-ethyl-4-methylimidazole, 1-(2-hydroxy-3-phenoxypropyl)-2-phenylimidazoline, 1-(2-hydroxy-3-butoxypropyl)-2-methylimidazoline, 2-(dimethylaminomethyl)phenol, 2,4,6-tris(dimethylaminomethyl)phenol, N-β-hydroxyethylmorpholine, 2-dimethylaminoethane thiol, 2-mercaptopyridine, 2-mercaptobenzoimidazole, 2-mercaptobenzothiazole, 4-mercaptopyridine, N,N-dimethylaminobenzoic acid, N,N-dimethylglycine, nicotinic acid, isonicotinic acid, picolinic acid, N,N-dimethylglycine hydrazide, N,N-dimethylpropionic acid hydrazide, nicotinic acid hydrazide, and isonicotinic acid hydrazide; and the like.

In order to further improve storage stability of the epoxy resin composition of the invention, an active hydrogen compound having two or more active hydrogen atoms in the molecule may be added as a third component, when the latent curing accelerator is produced. Examples of the activated hydrogen compound may include, but are not limited to: polyhydric phenols such as bisphenol A, bisphenol F, bisphenol S, hydroquinone, catechol, resorcinol, pyrogallol, and phenol novolak resin; polyhydric alcohols such as trimethylolpropane; polybasic carboxylic acids such as adipic acid and phthalic acid; 1,2-dimercaptoethane, 2-mercaptoethanol, 1-mercapto-3-phenoxy-2-propanol, mercaptoacetic acid, anthranilic acid, lactic acid, and the like.

Examples of the isocyanate compound, which is used as a surface treating agent in the production of the latent curing accelerator, may include: monofunctional isocyanate compounds such as n-butyl isocyanate, isopropyl isocyanate, phenyl isocyanate, and benzyl isocyanate; polyfunctional isocyanate compounds such as hexamethylenediisocyanate, toluylenediisocyanate, 1,5-naphthalenediisocyanate, diphenylmethane-4,4'-diisocyanate, isophoronediisocyanate, xylylenediisocyanate, p-phenylenediisocyanate, 1,3,6-hexamethylenetriisocyanate, and bicycloheptanetriisocyanate; and the like.

Instead of the polyfunctional isocyanate compounds described above, compounds containing isocyanate groups at the terminal ends thereof, obtained by reaction of the polyfunctional isocyanate compound described above with the active hydrogen compound may be used. Examples of such a compound may include addition reaction products having isocyanate groups at the terminal ends thereof, obtained by reaction of toluylenediisocyanate with trimethylolpropane; addition reaction products having isocyanate groups at the terminal ends thereof, obtained by reaction of toluylenediisocyanate with pentaerythritol; and the like.

The isocyanate compound used in the production of the latent curing accelerator as the surface treating agent, however, is not limited to the examples described above.

In addition, the acidic substance used in the production of the latent curing accelerator as the surface treating agent may be in any form of gas, liquid, and solid, and may be any of an inorganic acid and an organic acid. Examples thereof may include, but are not limited to: carbon dioxide gas, sulfurous acid gas, sulfuric acid, hydrochloric acid, oxalic acid, phosphoric acid, acetic acid, formic acid, propionic acid, adipic acid, caproic acid, lactic acid, succinic acid, tartaric acid, sebacic acid, p-toluenesulfonic acid, salicylic acid, boric acid, tannic acid, algic acid, polyacrylic acid, polymethacrylic acid, phenol, pyrogallol, phenol resins, resorcin resins, and the like.

The latent curing accelerator described above can be easily obtained by mixing the epoxy compound, the amine, and, if necessary, the activated hydrogen compound; reacting the mixture at a temperature of room temperature to 200° C.; and solidifying and pulverizing the resulting product, or reacting the mixture in a solvent such as methyl ethyl ketone, dioxane, or tetrahydrofuran; removing the solvent; and pulverizing the resulting solid matter.

Commercially available products may be used as the latent curing accelerator. Examples of the commercially available products may include, but are not limited to "Amicure PN-23" (trademark, Ajinomoto Co., Inc.), "Amicure PN-H" (trademark, Ajinomoto Co., Inc.), "Amicure MY-24" (trademark, Ajinomoto Co., Inc.), "Novacure HX-3742" (trademark, Asahi Kasei Corporation), "Novacure HX-3721" (trademark, Asahi Kasei Corporation), and the like.

The epoxy resin composition of the invention may contain, if necessary, various additives such as a filler, a diluent, a solvent, a pigment, a plasticity-imparting agent, a coupling agent, and an antioxidant.

When the epoxy resin composition of the invention contains an isocyanate group-containing compound as the additive, the adhesive force of the epoxy resin composition can be improved without remarkably impairing the curability thereof.

The isocyanate group-containing compound is not particularly limited, and examples thereof may include n-butylisocyanate, isopropyl isocyanate, 2-chloroethylisocyanate, phenylisocyanate, p-chlorophenylisocyanate, benzylisocyanate, hexamethylenediisocyanate, 2-ethylphenylisocyanate, 2,6-dimethylphenylisocyanate, 2,4-toluenediisocyanate, 2,6-toluenediisocyanate, 1,5-naphthalenediisocyanate, diphenylmethane-4,4'-diisocyanate, tolidinediisocyanate, isophoronediisocyanate, xylylenediisocyanate, p-phenylenediisocyanate, 1,3,6-hexamethylenetriisocyanate, bicycloheptanetriisocyanate, and the like.

The isocyanate group-containing compound is used usually in an amount within a range of 0.1 to 20 parts by weight based on 100 parts by weight of the epoxy resin.

According to the invention, a reaction product of a compound having one or more isocyanate groups in the molecule with a compound having at least one primary and/or secondary amino group in the molecule may also be used as the curing accelerator.

Such a curing accelerator can be obtained by reaction of the isocyanate compound having one or more isocyanate groups in the molecule with the compound having the primary and/or secondary amino group in an organic solvent such as dichloromethane.

Examples of the isocyanate compound having one or more isocyanate groups in the molecule may include, but are not limited to: n-butylisocyanate, isopropylisocyanate, 2-chloroethylisocyanate, phenylisocyanate, p-bromophenylisocyanate, m-chlorophenylisocyanate, o-chlorophenylisocyanate, p-chlorophenylisocyanate, 2,5-dichlorophenylisocyanate, 3,4-dichlorophenylisocyanate, 2,6-dimethylphenylisocyanate, o-fluorophenylisocyanate, p-fluorophenylisocyanate, m-tolylisocyanate, p-tolylisocyanate, o-trifluoromethylphenylisocyanate, m-trifluoromethylphenylisocyanate, benzylisocyanate, hexamethylenediisocyanate, 2,4-toluylenediisocyanate, 2,6-toluylenediisocyanate, 1,5-naphthalenediisocyanate, diphenylmethane-4,4'-diisocyanate, 2,2-dimethyldiphenylmethane-4,4'-diisocyanate, tolidinediisocyanate, isophoronediisocyanate, xylylenediisocyanate, 1,3-bis(isocyanatemethyl)cyclohexane, p-phenylenediisocyanate, 1,3,6-hexamethylenetriisocyanate, bicycloheptanetriisocyanate, tris(3-isocyanato-4-methylphenyl)isocyanurate, tris(6-isocyanatohexyl)isocyanurate, and the like.

Examples of the compound having at least one primary and/or secondary amino group in the molecule may include, but are not limited to: dimethylamine, diethylamine, di-n-propylamine, di-n-butylamine, di-n-hexylamine, di-n-octylamine, di-n-ethanolamine, dimethylaminopropylamine, diethylaminopropylamine, morpholine, piperidine, 2,6-dimethylpiperidine, 2,2,6,6-tetramethylpiperidine, piperazine, pyrrolidine, benzylamine, N-methylbenzylamine, cyclohexylamine, metaxylylenediamine, 1,3-bis(aminomethyl)cyclohexane, isophoronediamine, N-aminoethylpiperazine, 2-methylimidazole, 2-ethyl-4-methylimidazole, 2-undecylimidazole, 2-phenylimidazole, 1,1-dimethylhydrazine, and the like.

In the present invention, in addition to the above, examples of the curing accelerator may include the imidazoles and the tertiary amines described above, epoxy adducts of guanidine and microencapsulated guanidines, organophosphine compounds such as triphenylphosphine and tetraphenylphosphonium-tetraphenylborate, and the like.

In the epoxy resin composition according to the present invention, the curing accelerator, including the latent curing accelerator described above, is used in an amount usually of 0.05 to 10 parts by weight, preferably 0.1 to 10 parts by weight, based on 100 parts by weight of the epoxy resin. When the amount of the curing accelerator used is less than 0.05 parts by weight, curing failure may sometimes occur in the obtained epoxy resin composition; whereas when the amount of addition is more than 10 parts by weight, the effect of improving the cure acceleration has almost reached the ceiling, and the heat resistance and mechanical strength of the obtained epoxy resin composition may sometimes be impaired.

The epoxy resin composition according to the invention may further comprise, in addition to the components described above, a thermosetting resin or a conventional and common additive, depending on the application intended and the property required.

Examples of the thermosetting resin may include phenol resins, block isocyanate resins, xylene resins, a combination of radical-generating agents and polymerizable resins, and the like.

Examples of the additive may include: an inorganic filler such as barium sulfate, barium titanate, silicon oxide powder, amorphous silica, talc, cray, mica powder, aluminum hydroxide, or magnesium hydroxide; an organic filler such as silicone powder, nylon powder, or fluorine powder; a thickener such as asbestos, Orben, or Benton; a silicone-, fluorine-, or polymer-based defoaming agent; a leveling agent; an adhesion-imparting agent such as an imidazole, thiazol, triazole, or a silane coupling agent; a phosphorus flame retardant; and the like.

Furthermore, the epoxy resin composition of the invention may, comprise, if necessary, a known common coloring agent such as Phthalocyanine Blue, Phthalocyanine Green, Iodine Green, Disazo Yellow, titanium oxide, or carbon black may be contained.

(Use of Epoxy Resin Composition)

As described above, the epoxy resin composition of the invention is superior in hydrolysis resistance, heat resistance and moisture resistance to those conventionally known epoxy resin compositions, and thus it can be preferably used as an adhesive or a sealing agent. The adhesive according to the invention, accordingly, comprises the epoxy resin composition described above, and the sealing agent according to the invention comprises the epoxy resin composition described above.

The adhesive and sealing agent according to the invention may further contain an additive. Examples of the additive may include: a flow behavior controller such as silicic acid, magnesium silicate, or barium sulfate; a thermal conductivity-imparting agent such as alumina; a conductivity-imparting agent such as silver or carbon; a coloring agent such as a pigment or a dye; and the like. The additive can be mixed with the epoxy resin composition using a conventionally known common mixer such as a three-rollers milling machine or a planetary mixer.

The epoxy resin composition of the invention, in particular, can provide a cured product superior in heat resistance and adhesion with a plated conductor layer. Thus, an adhesive film, a prepreg, a laminate, and a multilayer printed circuit board obtained using such an epoxy resin composition are now explained in detail below.

First, the adhesive film according to the invention comprises a support base film, and a thin film formed from the epoxy resin composition of the invention on the support base film. The adhesive film can be obtained by forming the thin film of the epoxy resin composition on the support base film.

The adhesive film of the invention is obtained by coating a surface of the support base film with a resin varnish in which the epoxy resin composition is dissolved in an appropriate organic solvent; and then drying the solvent by heating and/or hot air spraying to form a thin film.

Examples of the support base film may include: a polyolefin film such as polyethylene film or polyvinyl chloride film; a polyester film such as polyethylene terephthalate film; polycarbonate film; polyimide film; a release paper; a metal foil such as copper foil or aluminum foil; and the like. The support base film may be subjected to a release treatment in addition to a mad (modification by accelerated diffusion) treatment and a corona treatment.

Examples of the organic solvent mentioned above may include: ketones such as acetone, methyl ethyl ketone, and cyclohexanone; acetic acid esters such as ethyl acetate, butyl acetate, cellosolve acetate, propyleneglycol monomethylether acetate, and carbitol acetate; cellosolves such as cellosolve and butyl cellosolve; carbitols such as carbitol and butyl carbitol; aromatic hydrocarbons such as toluene and xylene; dimethylformamide, dimethylacetamide; and the like. They may be used alone or as a mixture of two or more kinds.

More specifically, the adhesive film of the invention is prepared as follows. The epoxy resin composition layer having a thickness which is equal to or more than the thickness of a conductor of an inner layer circuit board to be laminated and which is within a range of 10 to 150 µm is provided on the support base film having a thickness of 10 to 200 µm, and a protective film having a thickness of 1 to 40 µm is laminated on the other side of the epoxy resin composition layer, and the resulting product is wound in a roll and stored.

The prepreg according to the invention comprises a sheet-shaped reinforcement substrate formed from fiber, and a semi-cured product formed from the epoxy resin composition of the invention which is coated on the substrate and/or with which the substrate is impregnated.

The prepreg of the invention can be obtained by coating the sheet-shaped reinforcement substrate formed from a fiber with the epoxy resin composition of the invention by a hot-melt coating method, or by immersing the sheet-shaped reinforcement substrate with the epoxy resin composition of the invention by a solvent method, and heating the resultant to semi-cure the epoxy resin composition.

As the sheet-shaped reinforcement substrate formed from the fiber, a known and commonly used fiber for a prepreg such as a glass cloth or an aramide fiber may be used. According to the hot-melt coating, the epoxy resin composition containing no solvent is once coated on a paper having good peeling-off property, followed by laminating the epoxy resin composition on the sheet-shaped reinforcement substrate, or alternatively the epoxy resin composition is directly coated on the sheet-shaped reinforcement substrate using a die coater In turn, according to the solvent method, the sheet-shaped reinforcement substrate is immersed in a resin varnish composed of the epoxy resin composition dissolved in an organic solvent to impregnate the substrate with the composition, and then the resulting product is dried, similarly in the production of the adhesive film.

The multilayer printed circuit board according to the invention comprises a cured layer of the epoxy resin composition of the invention, a plated conductor layer formed on a roughened surface of the cured layer of the epoxy resin, and a pattern-processed inner layer circuit board laminated closely to another surface of the cured layer of the epoxy resin.

In the production of the multilayer printed circuit board of the present invention, the pattern-processed inner layer circuit board is coated with the epoxy resin composition, drying is performed if an organic solvent is contained, and the resulting product is heat-cured. As the inner layer circuit; board, a glass epoxy board, a metal board, a polyester board, a polyimide board, a BT resin board, a thermosetting polyphenylene ether board, or the like may be used. The surface of the circuit may be in advance subjected to a roughening treatment. When the drying is performed, it is preferably performed at a temperature of 70 to 130° C. for 5 to 40 minutes. The heat-curing is preferably performed at a temperature of 130 to 180° C. for 15 to 90 minutes.

After curing by heating, if necessary, hole making is performed at pre-determined through hole parts or via hole parts using a drill and/or a laser, or plasma. Subsequently, the roughening treatment is performed using an oxidant such as a permanganate, dichromate, ozone, hydrogen peroxide/sulfuric acid, or nitric acid, thereby forming uneven anchors on the surface of the adhesive layer. Then, a conductor layer is formed by nonelectrolytic plating and/or electroplating. At that time, a plating resist having a pattern reverse to that of the conductor layer may be formed, and the conductor layer may be formed by the nonelectrolytic plating alone. After the conductor layer is formed as above, an annealing treatment is performed at 150 to 180° C. for 20 to 60 minutes to cure the unreacted epoxy resin remaining, whereby the peel strength of the conductor layer can be further improved.

In order to produce the multilayer printed circuit board using the epoxy resin composition of the invention, the support base film, and if necessary, the adhesive film provided with a protective film thereon, the adhesive film is laminated on the pattern-processed inner layer circuit board after the protective film has been removed. That is, the thin adhesive film of the epoxy resin composition of the adhesive film is laminated on the pattern-processed inner layer circuit board with heating and pressurizing. The lamination is performed as follows. The film and the inner layer circuit board are pre-heated, if necessary. The temperature is from 70 to 130° C., and the pressure is from 1 to 11 kgf/cm². The lamination is preferably performed under a reduced pressure. The lamination may be performed in a batch method or a continuous method using a roll.

After the lamination, the obtained product is cooled to around room temperature, and the support film is peeled off. Then, the epoxy resin composition is transferred on the inner layer circuit board, and cured by heating. When a support film which has been subjected to a release treatment is used, the support film may be peeled off after curing. Thereafter, the film surface is subjected to the roughening treatment with the oxidant in the same manner as above, and the conductor layer is formed by plating, thereby obtaining the multilayer printed circuit board.

Meanwhile, in order to produce the multilayer printed circuit board using the prepreg formed from the epoxy resin composition of the invention, one or, if necessary, several sheets of prepregs are put on the pattern-processed inner layer circuit board, a metal plate is put thereon through a releasing film, and the resulting laminate is pressed with pressurizing and heating, preferably at a temperature of 120 to 180° C. under a pressure of 5 to 40 kgf/cm² for 20 to 100 minutes. The production can be performed by the laminating method described above. Thereafter, the surface of the prepreg is subjected to the roughening treatment with the oxidant in the same manner as above, and the conductor layer is formed by plating, whereby the multilayer printed circuit board can be obtained.

The obtained multilayer printed circuit board has an insulating layer, which is the cured product of the epoxy resin composition of the invention, between the inner layer circuits, when the inner layer circuit board has two or more layers of the pattern-processed inner layer circuits in the same direction.

The pattern-processed inner layer circuit board in the invention is a naming relative to the multilayer printed circuit board. For example, when circuits are formed on both surfaces of a substrate, insulating layers of the thin films of the cured epoxy resin composition are formed on the surfaces of the two circuits, and then circuits are further formed on the two surfaces, then a four-layer printed circuit board is formed.

In this case, the inner layer circuit board is a printed circuit board which is formed on the substrate and in which the circuits are formed on the both surfaces. When one layer circuit is additionally formed through an insulating layer on each surface of the four-layer printed circuit board, then a six-layer printed circuit board is formed. In this case, the inner layer circuit board is the four-layer printed circuit board.

The laminate of the invention is obtained by coating a surface of a both-face copper clad laminate from which a copper foil is etched out or at least one surface of an unclad plate with the epoxy resin composition of the invention, and curing it by heating. The unclad plate is obtained by using a releasing film instead of a copper foil during the production of the copper clad laminate.

The thus obtained laminate is subjected to the roughening treatment with the oxidant such as permanganate, dichromate, ozone, hydrogen peroxide/sulfuric acid, or nitric acid, thereby forming uneven anchors on the surface of the laminate. Then, a conductor layer can be directly formed on the laminate surface by nonelectrolytic plating and/or electroplating.

The laminate of the invention can also be obtained by laminating the adhesive film formed from the epoxy resin composition on a surface of a both-face copper clad laminate from which a copper foil is etched out or at least one surface of an unclad plate, and curing it by heating.

The thus obtained laminate is subjected to the roughening treatment with the oxidant such as permanganate, dichromate, ozone, hydrogen peroxide/sulfuric acid, or nitric acid, thereby forming uneven anchors on the surface of the laminate. Then, a conductor layer can be directly formed on the laminate surface by nonelectrolytic plating and/or electroplating.

The laminate of the invention can also be obtained by putting the predetermined number of sheets of prepregs formed from the epoxy resin composition of the invention on top of one another, or putting the prepreg on a surface of a both-face copper clad laminate from which a copper foil is etched out or at least one surface of an unclad plate, putting a metal plate thereon through a releasing film, and pressing the laminate with pressurizing and heating.

The thus obtained laminate is subjected to the roughening treatment with the oxidant such as permanganate, dichromate, ozone, hydrogen peroxide/sulfuric acid, or nitric acid, thereby forming uneven anchors on the surface of the laminate. Then, a conductor layer can be directly formed on the laminate surface by nonelectrolytic plating and/or electroplating.

EXAMPLES

The present invention is explained by means of Examples below, but the invention is not particularly limited to Examples.

(Synthesis of Allylglycoluril)

In the following, thioacetic acid manufactured by Tokyo Chemical Industry Co., Ltd., azobisisobutyronitrile manufactured by Sigma-Aldrich Co. Llc, thionyl chloride and sodium borohydride manufactured by Wako Pure Chemical Industries, Ltd., and a 40% aqueous disodium trithiocarbonate solution manufactured by BOC Sciences, were used.

Reference Example 1

Synthesis of 1,3,4,6-tetraallylglycoluril

Synthesis was performed according to a method described in JP-A No. H11-171887.

14.2 g (100 mmol) of glycoluril, 16.0 g (400 mmol) of sodium hydroxide, and 140 mL of dimethyl sulfoxide were mixed, and the mixture was heated at a temperature of 40° C. for one hour with stirring. Thereafter, 34.4 g (400 mmol) of allyl chloride was added dropwise at the same temperature as above over a time of 20 minutes. After the addition was finished, the mixture was further heated at a temperature of 40° C. for two hours with stirring to complete the reaction.

The obtained reaction mixture was dried under a reduced pressure to dryness. The obtained dried cake was separated and extracted using 400 mL of ethyl acetate and 400 mL of water. After the ethyl acetate layer was washed with 100 mL of water, followed by 100 mL of a saturated saline solution, the resulting product was dried on anhydrous sodium sulfate, and ethyl acetate was distilled away therefrom under a reduced pressure to obtain 27.4 g of 1,3,4,6-tetraallylglycoluril as colorless oil. Yield: 90%.

Reference Example 2

Synthesis of 1,3,4,6-tetraallkyl-3a,6a-dimethylglycoluril

Synthesis was performed according to a method described in JP-A No. H11-171887.

17.0 g (100 mmol) of 3a,6a-dimethylglycoluril, 16.0 g (400 mmol) of sodium hydroxide, and 150 mL of dimethyl sulfoxide were mixed, and the mixture was heated at a temperature of 40° C. for one hour. Thereafter, 34.4 g (400 mmol) of allyl chloride was added dropwise at the same temperature as above over a time of 20 minutes. After the addition was finished, the mixture was further heated at a temperature of 40° C. for two hours to complete the reaction. Thereafter, the same post-treatment as in Reference Example 1 was performed to obtain 26.1 g of 1,3,4,6-tetraallyl-3a,6a-dimethylglycoluril as crystals. Yield: 79%.

Reference Example 3

Synthesis of 1,3-Diallylglycoluril

To a 100 mL flask equipped with a thermometer were added 3.00 g (50.0 mmol) of urea and 8.71 g (60.0 mmol) of a 40% aqueous glyoxal solution. To the mixture was added 2 drops of a 40% aqueous sodium hydroxide solution at room temperature, and the mixture was stirred at a temperature of 80° C. for one hour. Subsequently, the reaction mixture was concentrated under a reduced pressure. Into the obtained concentrate were 7.00 g (50.0 mmol) of diallyl urea, 50 mL of acetic acid, and 490 mg (5.0 mmol) of sulfuric acid, and the mixture was stirred overnight at a temperature of 110° C. Subsequently, the reaction mixture was cooled to room temperature, to which 50 mL of acetone was added, and precipitated crystals were filtered and dried to obtain 1,3-diallylglycoluril as white viscous oil. Yield: 39%.

IR spectrum of the obtained 1,3-diallylglycoluril is shown in FIG. 1. The δ values in the $^1$H-NMR spectrum (d6-DMSO) are as follows:

7.52 (s, 2H), 5.69-5.84 (m, 2H), 5.08-5.23 (m, 6H), 3.92-3.97 (m, 2H), 3.52 (dd, 2H)

Synthesis of mercaptoalkylglycoluril

Example 1

Synthesis of 1,3-bis(3-mercaptopropyl)glycoluril

In a 50 mL flask equipped with a thermometer were put 560 mg (2.5 mmol) of 1,3-diallylglycoluril, 457 mg (6.0 mmol) of thioacetic acid, and 10 mL of tetrahydrofuran, to which 25 mg (0.15 mmol) of azobisisobutyronitrile was added, and then the reaction was performed at a temperature of 60° C. over a period of 16 hours while the mixture was stirred.

After the obtained reaction mixture was cooled, it was concentrated under a reduced pressure, and to the obtained concentrate was added 10 mL of methanol. To the obtained mixture was added 189 mg (5.0 mmol) of sodium borohydride at room temperature, and then the stirring was continued at 60° C. through the night. After the reaction was finished, the reaction mixture was cooled to 5° C., to which 30 mL of a saturated aqueous ammonium chloride solution was added, and then the stirring was continued for 30 minutes.

The obtained reaction mixture was subjected to an extraction treatment with 30 mL of chloroform, and the obtained organic layer was washed with 15 mL of water three times. The obtained organic layer was concentrated under a reduced pressure to obtain 336 mg of 1,3-bis(3-mercaptopropyl)glycoluril as brown oil. Yield: 46%.

Figure 2:
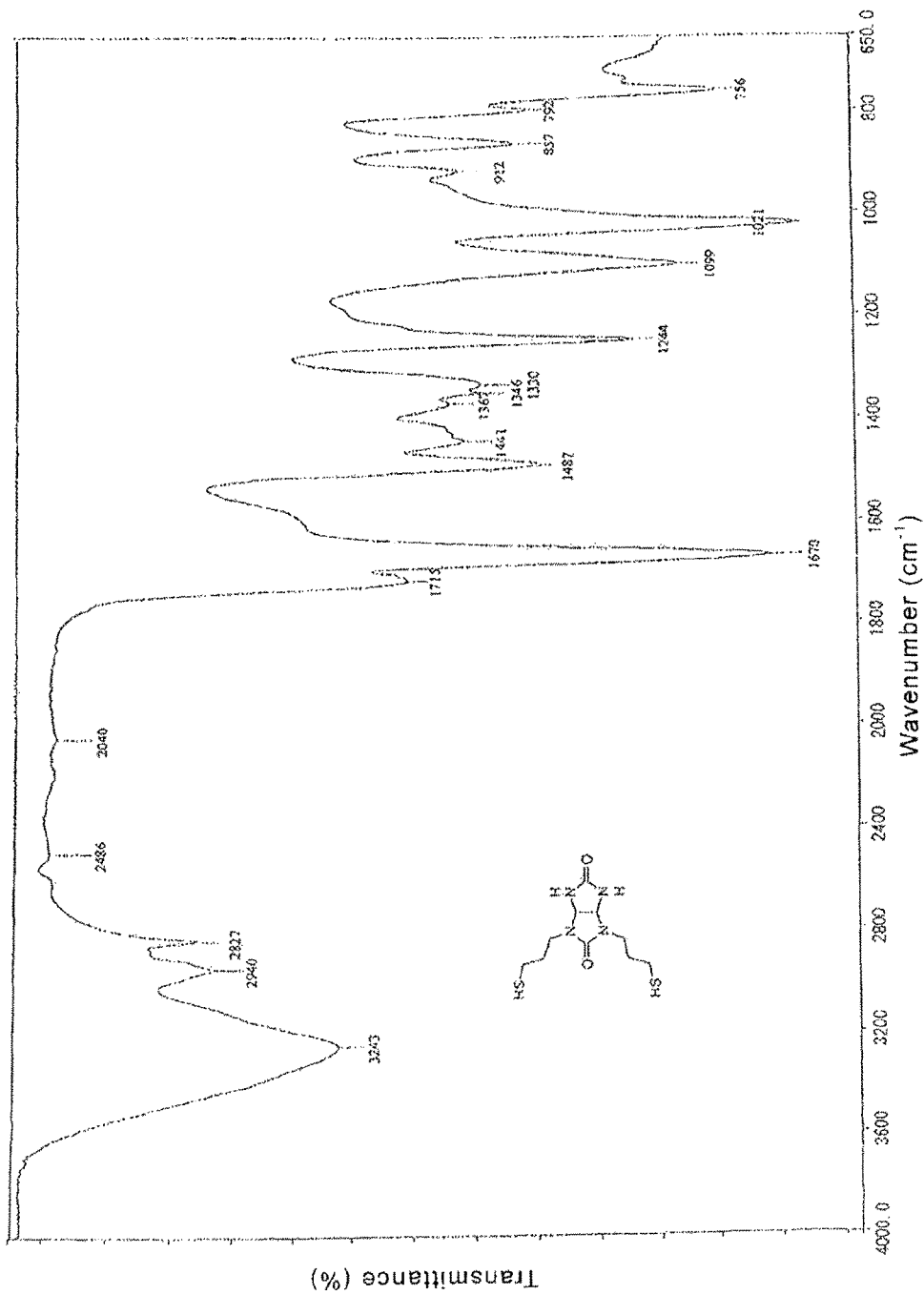
FIG. 2 shows IR spectrum of 1,3-bis(3-mercaptopropyl) glycoluril.

IR spectrum of the obtained 1,3-bis(3-mercaptopropyl) glycoluril is shown in FIG. 2. The δ values in the $^1$H-NMR spectrum (d6-DMSO) are as follows:

7.52 (br, 2H), 5.27 (s, 2H), 3.22-3.35(m, 4H), 2.65-2.89 (m, 4H), 1.72-1.90 (m, 4H)

Example 2

Synthesis of 1,3,4,6-tetrakis(3-mercaptopropyl)glycoluril

In a 100 mL flask equipped with a thermometer were put 3.02 g (10.0 mmol) of 1,3,4,6-tetraallyl glycoluril, 3.65 g (48.0 mmol) of thioacetic acid, and 20 mL of tetrahydrofuran, to which 66 mg (0.4 mmol) of azobisisobutyronitrile was added, and then the reaction was performed at a temperature of 60° C. for 18 hours while the mixture was stirred.

After the obtained reaction mixture was cooled, it was concentrated under a reduced pressure, and to the obtained concentrate was added 20 mL of methanol. To the obtained mixture was added 1.51 g (40.0 mmol) of sodium borohydride at room temperature, and then the stirring was continued at a temperature of 60° C. through the night.

After the reaction was finished, the reaction mixture was cooled to 5° C., to which 30 mL of a saturated aqueous ammonium chloride solution was added, and then the stirring was continued for 30 minutes. The obtained reaction mixture was subjected to an extraction treatment with 30 mL of chloroform, and the obtained organic layer was washed with 15 mL of water three times. The obtained organic layer was concentrated under a reduced pressure to obtain 3.12 g of 1,3,4,6-tetrakis(3-mercaptopropyl)glycoluril as pale yellow oil. Yield: 65%.

Figure 3:
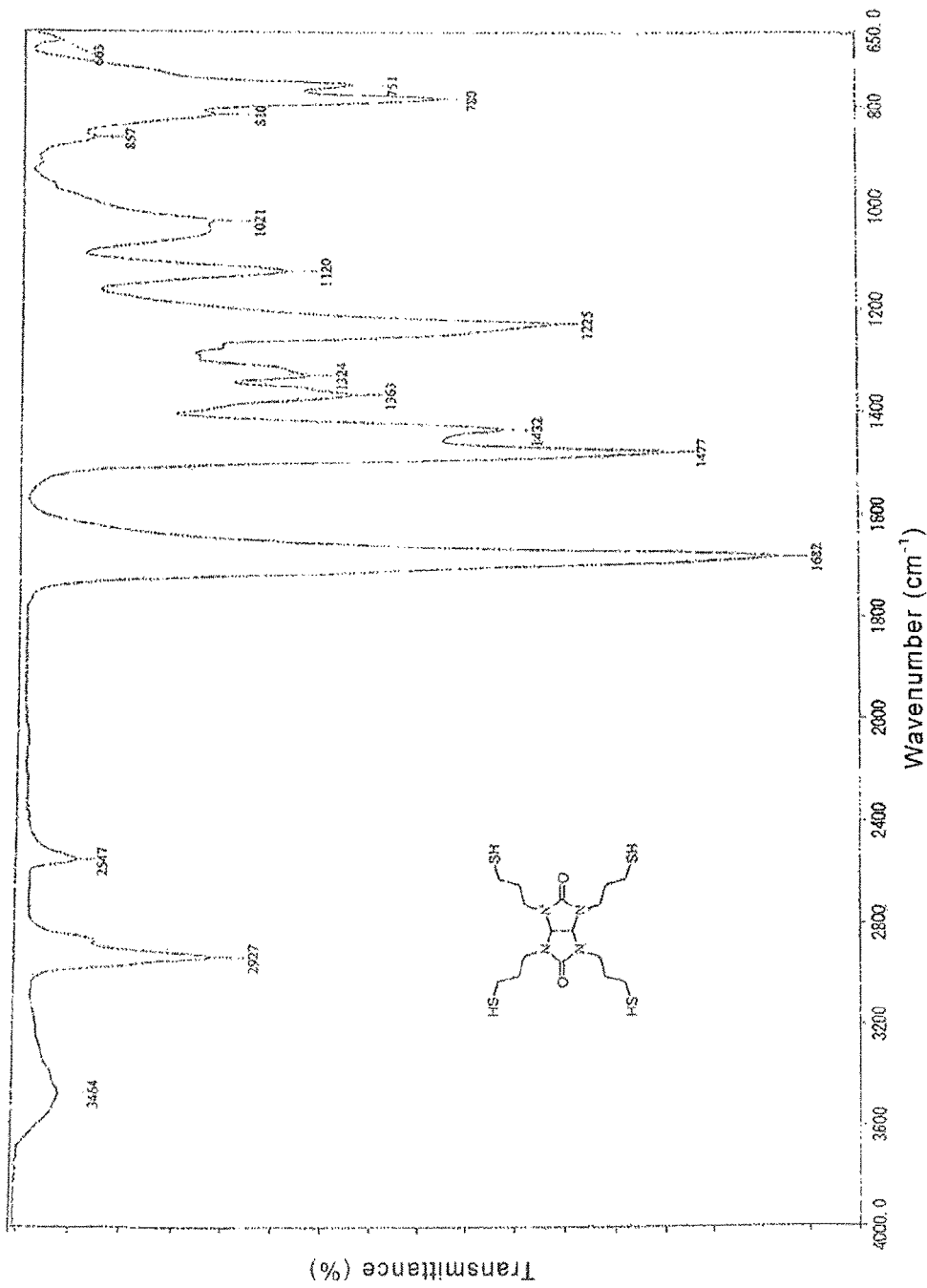
FIG. 3 shows IR spectrum of 1,3,4,6-tetrakis(3-mercaptopropyl)-glycoluril.

IR spectrum of the obtained 1,3,4,6-tetrakis(3-mercaptopropyl)glycoluril is shown in FIG. 3. The δ values in the $^1$H-NMR spectrum (d6-DMSO) are as follows:

5.32 (s, 2H), 3.43-3.50 (m, 4H), 3.12-3.20 (m, 4H), 2.43-2.51 (m, 8H), 1.69-1.86 (m, 8H)

Example 3

Synthesis of 1,3,4,6-tetrakis(3-mercaptopropyl)-3a,6a-dimethylglycoluril

In a 100 mL flask equipped with a thermometer were put 3.30 g (10.0 mmol) of 1,3,4,6-tetraallyl-3a,6a-dimethylglycoluril, 3.65 g (48.0 mmol) of thioacetic acid, and 20 mL of tetrahydrofuran, to which 66 mg (0.4 mmol) of azobisisobutyronitrile was added, and then the reaction was performed at a temperature of 60° C. for 18 hours while the mixture was stirred.

After the obtained reaction mixture was cooled, it was concentrated under a reduced pressure, and to the obtained concentrate was added 20 mL of methanol. To the obtained mixture was added 1.51 g (40.0 mmol) of sodium borohydride at room temperature, and then the stirring was continued at a temperature of 60° C. through the night. After the reaction was finished, the reaction mixture was cooled to a temperature of 5° C., to which 30 mL of a saturated aqueous ammonium chloride solution was added, and then the stirring was continued for 30 minutes. The obtained reaction mixture was subjected to an extraction treatment with 30 mL of chloroform, and the obtained organic layer was washed with 15 mL of water three times. The obtained organic layer was concentrated under a reduced pressure to obtain 2.17 g of 1,3,4,6-tetrakis(3-mercaptopropyl)-3a,6a-dimethylglycoluril as pale yellow oil. Yield: 46%.

Figure 4:
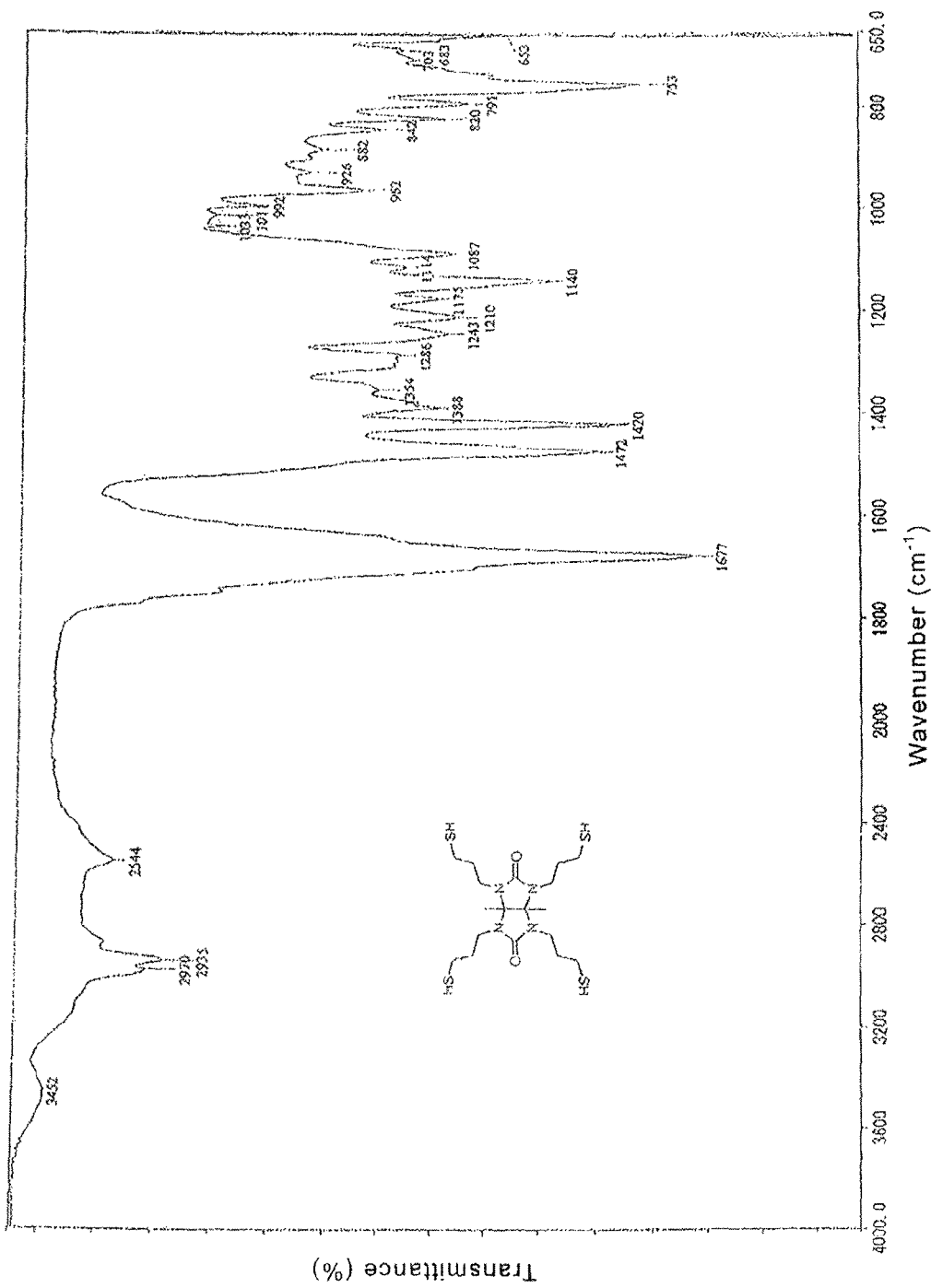
FIG. 4 shows IR spectrum of 1,3,4,6-tetrakis(3-mercaptopropyl)-3a,6a-dimethylglycoluril.

IR spectrum of the obtained 1,3,4,6-tetrakis(3-mercaptopropyl)-3a,6a-dimethylglycoluril is shown in FIG. 4. The δ values in the $^1$H-NMR spectrum (d6-DMSO) are as follows:

3.31-3.42 (m, 8H), 2.47-2.59 (m, 8H), 1.82-1.89 (min, 8H), 1.53 (t, 4H), 1.47 (s, 6H)

Example 4

Synthesis of 1,3,4,6-tetrakis(2-mercaptoethyl)glycoluril

In a 50 mL flask equipped with a thermometer were put 3.18 g (10.0 mmol) of 1,3,4,6-tetrakis(2-hydroxyethyl)glycoluril and 4.76 g (40.0 mmol) of thionyl chloride, and then the reaction was performed at a temperature of 70° C. for 5 hours while the mixture was stirred.

The obtained reaction mixture was concentrated under a reduced pressure, and to the obtained concentrate was added 20 mL of water. To the obtained mixture was added dropwise 15.4 g (40.0 mmol) of a 40% aqueous disodium trithiocarbonate solution at room temperature, and then the stirring was continued at a temperature of 100° C. for 6 hours. After the reaction was finished, the reaction mixture was cooled to 5° C., to which 50 mL of chloroform was added, and then the stirring was continued for 30 minutes. From the mixture was removed an aqueous layer, and the obtained organic layer was concentrated under a reduced pressure to obtain 3.26 g of 1,3,4,6-tetrakis(2-mercaptoethyl)glycoluril as yellow oil. Yield: 85%.

Figure 5:
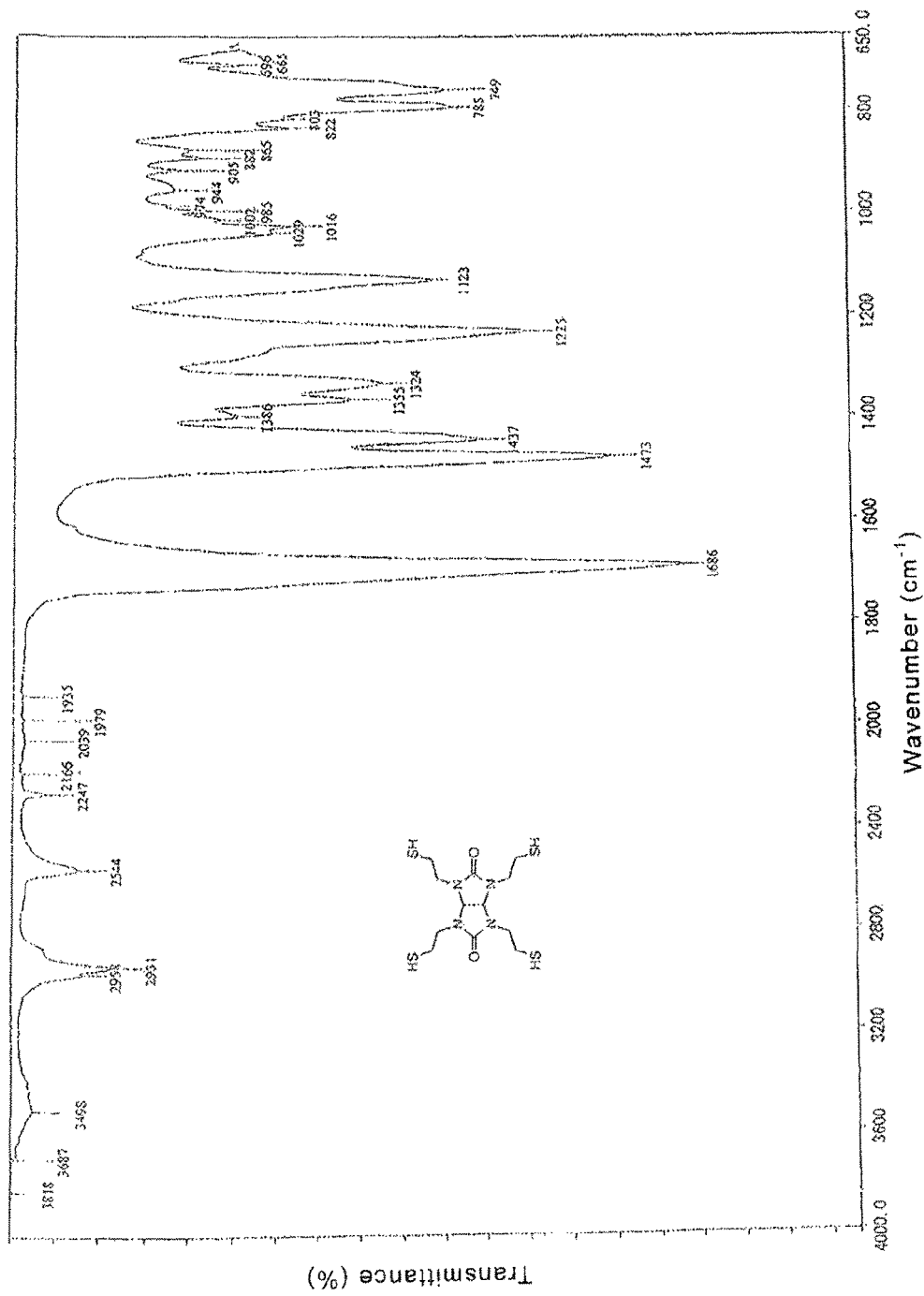
FIG. 5 shows IR spectrum of 1,3,4,6-tetrakis(2-mercaptoethyl)-glycoluril.

IR spectrum of the obtained 1,3,4,6-tetrakis(2-mercaptoethyl)-glycoluril is shown in FIG. 5. The δ values in the $^1$H-NMR spectrum (CDCl$_3$) are as follows:

5.55 (s, 2H), 3.71-3.78 (m, 4H), 3.31-3.39 (m, 4H), 2.83-2.92 (m, 4H), 2.67-2.76 (m, 4H), 1.46 (t, 4H)

(Preparation of Epoxy Resin Composition)

In the following, an epoxy resin ("jER 828" manufactured by Mitsubishi Chemical Corporation) was blended with the 1,3,4,6-tetrakis(3-mercaptopropyl)glycoluril obtained in Example 2, or the 1,3,4,6-tetrakis(2-mercaptoethyl)glycoluril obtained in Example 4 as the curing agent, and a solid dispersion type amine adduct latent curing accelerator ("Amicure PN-23" manufactured by Ajinomoto Fine-Techno Co., Inc.) as the curing accelerator to prepare an epoxy resin composition.

For comparison, an epoxy resin composition was prepared in the same manner as above except that as the curing agent, 1,3,5-tris-(3-mercaptobutyryloxyethyl)-1,3,5-triazine-2,4,6(1H,3H,5H)-trione ("Karenz MT NR1" manufactured by Showa Denko K. K., hereinafter referred to as the thiol compound (1)), represented by the following formula (I):

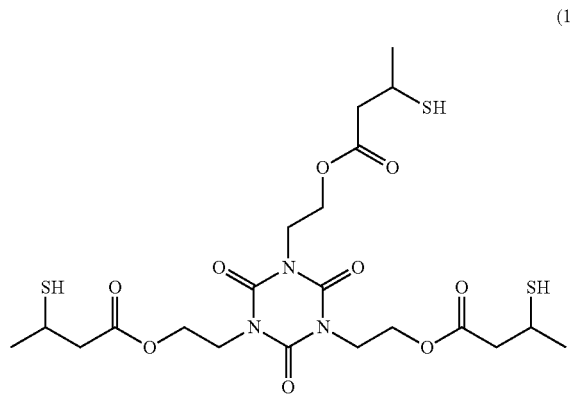

(1)

or trimethylolpropane tris(3-mercaptopropionate) ("TMMP" manufactured by SC Organic Chemical Co., Ltd., hereinafter referred to as the thiol compound (2)), represented by the following formula (2):

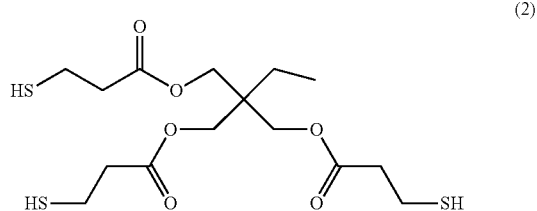 [SMILES: CCC(COC(=O)CCS)(COC(=O)CCS)COC(=O)CCS]

(2)

was used.

Example 5

An epoxy resin composition was prepared by mixing 100 parts by weight of the epoxy resin with 64 parts by weight of the 1,3,4,6-tetrakis-(3-mercaptopropyl)glycoluril and 3 parts by weight of the latent curing accelerator.

Example 6

An epoxy resin composition was prepared by mixing 100 parts by weight of the epoxy resin with 56 parts by weight of the 1,3,4,6-tetrakis-(2-mercaptoethyl)glycoluril and 3 parts by weight of the latent curing accelerator.

Comparative Example 1

An epoxy resin composition was prepared in the same manner as in Example 5 except that 107 parts by weight of the thiol compound (1) was used instead of 64 parts by weight of 1,3,4,6-tetrakis(3-mercaptopropyl)glycoluril.

Comparative Example 2

An epoxy resin composition was prepared in the same manner as in Example 5 except that 75 parts by weight of the thiol compound (2) was used instead of 64 parts by weight of 1,3,4,6-tetrakis(3-mercaptopropyl)glycoluril.

(Measurement of Glass Transition Temperature of Cured Product of Epoxy Resin Composition)

The glass transition temperature (Tg) of the cured product of each epoxy resin composition obtained in Examples 5 and 6 and Comparative Examples 1 and 2 were measured using a differential scanning calorimeter ("EXSTAR 6000" manufactured by SII Nano Technology Inc.). The epoxy resin composition was heated at a temperature rising rate of 10° C./minute from 30° C. to 270° C. for curing, subsequently the obtained cured product was cooled at a temperature falling rate of −50° C./minute from 270° C. to 10° C., and then it was heated at a temperature rising rate of 10° C./minute from 10° C. to 100° C., whereby a glass transition temperature of the cured product was measured. The results are shown in Table 1.

TABLE 1

| | Example | | Comparative Example | |
|---|---|---|---|---|
| | 5 | 6 | 1 | 2 |
| Curing agent | 1,3,4,6-Tetrakis(3-mercaptopropyl)glycoluril | 1,3,4,6-Tetrakis(2-mercaptoethyl)glycoluril | Thiol compound (1) | Thiol compound (2) |
| Cured product Tg (° C.) | 93 | 100 | 36 | 32 |

It is shown that as the cured product of the epoxy resin composition of the invention comprises 1,3,4,6-tetrakis(3-mercaptopropyl)glycoluril or 1,3,4,6-tetrakis(2-mercaptoethyl)glycoluril as the curing agent, it was found to have a higher glass transition temperature than, and thus found to be superior in heat resistance to the cured product of the epoxy resin composition containing the thiol compound (1) or the thiol compound (2) as the curing agent.

Example 7

100 parts by weight of a bisphenol A epoxy resin (jER 828 manufactured by Mitsubishi Chemical Corporation, Epoxy equivalent: 185), and 55 parts by weight of tetrakis(mercaptoethyl)glycoluril were dissolved with stirring and heating, and then the mixture was cooled to room temperature. Subsequently 0.8 parts by weight of 2-phenyl-4,5-bis(hydroxymethyl)imidazole (2PHZ-PW manufactured by Shikoku Chemicals Corporation), 2 parts by weight of fine pulverized silica, and 0.5 parts by weight of a silicone defoaming agent were added thereto to prepare an epoxy resin composition.

The obtained epoxy resin composition was applied on a glass epoxy both-face copper clad laminate having a copper foil with a thickness of 35 μm, and was cured by heating at a temperature of 170° C. for 30 minutes. Then, the resin layer surface was subjected to a roughening treatment with an alkaline oxidant of permanganate, followed by nonelectrolytic plating and electroplating, and a printed circuit board was produced according to a subtractive method. After that, the resulting printed circuit board was heated (annealing treatment) at a temperature of 170° C. for 30 minutes, and the obtained product was used as a test piece.

The obtained test piece was subjected to measurement of a peel strength and a heat resistance test by boiling as described below. The results are shown in Table 2.
(Measurement of Peel Strength)

The measurement was performed in accordance with JIS C 6481. The conductor plating thickness was about 30 μm.
(Heat Resistance Test by Boiling)

After the test piece was boiled for 2 hours, it was immersed in a solder bath having a temperature of 260° C. for 30 seconds, and the appearance was visually observed. The evaluation was performed according to the following criteria:

◯: Excellent, x: Occurrence of swelling, peeling-off, or measling

Comparative Example 3

A test piece was produced in the same manner as in Example 7 except that 30 parts by weight of a phenol novolak resin ("Phenolite" manufactured by DIC Corporation) was used instead of tetrakis(mercaptoethyl)glycoluril.

The test piece was subjected to the measurement test of the peel strength and the heat resistance test by boiling in the same manner as in Example 7. The results are shown in Table 2.

TABLE 2

|  | Example 7 | Comparative Example 3 |
| --- | --- | --- |
| Measurement test of peel strength (kgf/cm) | 1.1 | 0.5 |
| Heat resistance best by boiling | ◯ | x |

According to the results shown in Table 2, the use of the epoxy resin composition of the invention was found to provide a multilayer printed circuit board which has a high peel strength and which is superior in heat resistance.

The invention claimed is:

1. An epoxy resin composition comprising an epoxy resin and a mercaptoalkylglycoluril represented by the following formula,

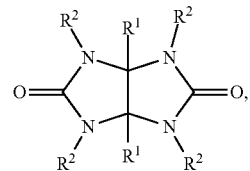

wherein $R^1$ represents a hydrogen atom, a lower alkyl group or a phenyl group; and $R^2$ represents a 2-mercaptoethyl group or a 3-mercaptopropyl group.

2. The epoxy resin composition according to claim 1, which further comprises a curing accelerator.

3. The epoxy resin composition according to claim 2, wherein the curing accelerator is an amine.

4. The epoxy resin composition according to claim 2, wherein the curing accelerator is a reaction product of an amine with an epoxy compound.

5. The epoxy resin composition according to claim 2, wherein the curing accelerator is a reaction product of a compound having one or more isocyanate groups in the molecule with a compound having at least one primary and/or secondary amino group in the molecule.

6. An adhesive comprising the epoxy resin composition according to claim 1.

7. A sealing agent comprising the epoxy resin composition according to claim 1.

8. An adhesive film comprising a support base film and a thin film of the epoxy resin composition according to claim 1 formed on the support base film.

9. A method for producing a multilayer printed circuit board comprising the steps of: laminating the adhesive film according to claim 8 on a pattern-processed inner layer circuit board with pressurizing and heating; curing the epoxy resin composition by heating while the support base film is peeled off or is not peeled off; roughening a surface of the obtained cured product with an oxidant; and forming a conductor layer on the roughened surface by plating.

10. A method for producing a multilayer printed circuit board comprising the steps of: coating a pattern-processed inner layer circuit board with the epoxy resin composition according to claim 1; curing the epoxy resin composition by heating; roughening a surface of the obtained cured product with an oxidant; and forming a conductor layer on the roughened surface by plating.

* * * * *